(12) United States Patent
Braun et al.

(10) Patent No.: US 6,821,739 B2
(45) Date of Patent: Nov. 23, 2004

(54) **METHODS OF DIAGNOSING AND TREATING CROHN'S DISEASE USING *PSEUDOMONAS* ANTIGENS**

(75) Inventors: Jonathan Braun, Tarzana, CA (US); Bo Wei, Los Angeles, CA (US); Ashley Forbes, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 237 days.

(21) Appl. No.: 09/976,451

(22) Filed: Oct. 12, 2001

(65) Prior Publication Data

US 2002/0068313 A1 Jun. 6, 2002

Related U.S. Application Data

(60) Provisional application No. 60/240,347, filed on Oct. 13, 2000.

(51) Int. Cl.[7] .................. G01N 33/53; G01N 33/537; G01N 33/554; G01N 33/567; G01N 33/569

(52) U.S. Cl. .................. 435/7.1; 435/7.2; 435/7.32; 435/7.92

(58) Field of Search .................. 435/7.1, 7.2, 7.32, 435/7.92

(56) References Cited

U.S. PATENT DOCUMENTS

| | | | | |
|---|---|---|---|---|
| 4,879,213 A | * | 11/1989 | Fox et al. .................. | 435/5 |
| 5,932,429 A | * | 8/1999 | Targan et al. .............. | 435/7.24 |
| 6,033,864 A | | 3/2000 | Braun et al. | |
| 6,309,643 B1 | | 10/2001 | Braun et al. | |

FOREIGN PATENT DOCUMENTS

| | | |
|---|---|---|
| WO | WO 99/45955 | 9/1999 |
| WO | WO 00/66067 | 11/2000 |

OTHER PUBLICATIONS

Salgaller et al (Cancer Immunol. Immunother. vol. 39, pp 105–116, 1994).*

Abe et al., "Clinical role for a superantigen in *Yersinia pseudotuberculosis* infection," *J. Clin. Invest.* 99:1823–1830 (1997).

Ambrose et al., "Antibiotic therapy for treatment in relapse of intestinal Crohn's disease. A prospective randomized study," *Dis. Colon Rectum* 28:81–85 (1985).

Aranda et al, "Analysis of intestinal lymphocytes in mouse colitis mediated by transfer of CD4+, CD45RB[high] T cells to SCID recipients," *J. Immunol.* 158:3464–3473 (1997).

Blaser et al., "Patients With Active Crohn's Disease Have Elevated Serum Antibodies to Antigens of Seven Enteric Bacterial Pathogens," *Gastroenterology* 87:888–894 (1984).

Blumberg et al., "Animal models of mucosal inflammation and their relation to human inflammatory bowel disease," *Curr. Opin. Immunol.* 11:648–656 (1999).

Brandwein et al., "Spontaneously colitic C3H/HeJBir mice demonstrate selective antibody reactivity to antigens of the enteric bacterial flora," *J. Immunol.* 159:44–52 (1997).

Bregenholt et al., "T–cell transfer and cytokine TCR gene deletion models in the study of inflammatory bowel disease," *APMIS* 105:655–662 (1997).

Brennan et al., "*Pseudomonas aeruginosa* outer–membrane protein F epitopes are highly immunogenic in mice when expressed on a plant virus," *Microbiology* 145:211–20 (1999).

Cachia et al., "The use of synthetic peptides in the design of a consensus sequence vaccine for *Pseudomonas aeruginosa*," *J. Pept. Res.* 52:289–99 (1998).

Callanan et al., "Regulation of the iron uptake genes in *Pseudomonas fluorescens* M114 by pseudobactin M114: the pbrA sigma factor gene does not mediate the siderophore regulatory response," *FEMS Microbiol. Lett.* 144:61–66 (1996).

Campbell et al., "Interaction of the receptor binding domains of *Pseudomonas aeruginosa* pili strains PAK, PAO, KB7 and P1 to a cross–reactive antibody and receptor analog: implications for synthetic vaccine design," *J. Mol. Biol.* 267:382–402 (1997).

Cellier et al., "*Mycobacterium paratuberculosis* and *Mycobacterium avium* subsp. *silvaticum* DNA cannot be detected by PCR in Crohn's disease tissue," *Gastroenterol. Clin. Biol.* 22:675–678 (1998).

Chen et al., "Recombinant protein composed of *Pseudomonas exotoxin* A, outer membrane proteins I and F as vaccine against *P. aeruginosa* infection," *Appl. Microbiol. Biotechnol.* 52:524–33 (1999).

Chiba et al., "No *Mycobacterium paratuberculosis* detected in intestinal tissue, including Peyer's patches and lymph follicles, of Crohn's disease," *J. Gastroenterology* 33:482–487 (1998).

Cho–Chung, "Antisense oligonucleotide inhibition of serine/threonine kinases: an innovative approach to cancer treatment," *Pharmacol. Ther.* 82:437–449 (1999).

(List continued on next page.)

Primary Examiner—Mark Navarro
(74) Attorney, Agent, or Firm—McDermott, Will & Emery LLP

(57) ABSTRACT

The present invention provides a method of identifying an agent useful in treating Crohn's disease. This method is practiced by culturing *P. fluorescens* under conditions that support growth; contacting the *P. fluorescens* with an agent; and assaying for reduced growth or viability of the *P. fluorescens* as compared to the growth or viability in the absence of the agent, where the reduced growth or viability of the *P. fluorescens* indicates that the agent is an anti-*P. fluorescens* agent useful in treating Crohn's disease. Also provided by the invention is a method of preventing or treating Crohn's disease in an individual by administering to the individual an effective dose of an anti-*Pseudomonas* vaccine.

8 Claims, 7 Drawing Sheets

OTHER PUBLICATIONS

Clarkston et al., "Role of *Mycobacterium paratuberculosis* in Crohn's Disease," *Dis. Colon Rectum* 41:195–199 (1998).

Cocito et al., "Paratuberculosis," *Clinical Microbiology Reviews* 7:328–345 (1994).

Cong et al., "CD4+ T cells reactive to enteric bacterial antigens in spontaneously colitic C3H/HeJBir mice: Increased T helper cell type 1 response and ability to transfer disease," *J. Exp. Med.* 187:855–864 (1998).

Cripps et al., "Vaccine strategies against *Pseudomonas aeruginosa* infection in the lung," *Behring Inst. Mitt.* 98:262–268 (1997).

Cryz et al., "Synthesis and characterization of a polyvalent *Escherichia coli* O–polysaccharide–toxin A conjugate vaccine," *Vaccine* 13:449–453 (1995).

Dalwadi et al., "Identification of a novel IBD–Associated microbial agent by representational difference analysis," *Gastroenterology* 116(4) : A696 AGA Abstracts (1999).

Dalwadi et al., "The Crohn's disease–associated bacterial protein, I2, is a novel enteric T cell superantigen" *Immunity* 15:149–58 (2001).

Del Prete et al., "Detection of *Mycobacterium paratuberculosis* in stool samples of patients with inflammatory bowel disease by IS900–based PCR and colorimetric detection of amplified DNA," *J. Microbiol. Methods* 33:105–114 (1998).

Dianda et al., "T cell receptor–αβ–deficient mice fail to develop colitis in the absence of a microbial environment," *Am. J. Pathol.* 150:91–97 (1997).

Doring and Dorner, "A multicenter vaccine trial using the *Pseudomonas aeruginosa* flagella vaccine IMMUNO in patients with cystic fibrosis," *Behring Inst. Mitt.* 98:338–344 (1997).

El–Zaatari et al., "Characterization of a Specific *Mycobacterium paratuberculosis* Recombinant Clone Expressing 35,000–Molecular–Weight Antigen and Reactivity with Sera from Animals with Clinical and Subclinical Johne's Disease," *Journal of Clinical Microbiology* 35:1794–1799 (1997).

Elsaghier et al., "Antibodies to *Mycobacterium paratuberculosis*–specific protein antigens in Crohn's disease," *Clin. Exp. Immunol.* 90:503–508 (1992).

Epelman et al., "*Pseudomonas aeruginosa* exoenzyme S induces transcriptional expression of proinflammatory cytokines and chemokines," *Infect. Immun.* 68:4811–4814 (2000).

Fidler et al., "Specific detection of *Mycobacterium paratuberculosis* DNA associated with granulomatous tissue in Crohn's disease," *Gut* 35:506–510 (1994).

Finegold and Sutter, "Fecal flora in different populations, with special reference to diet," *Am. J. Clin. Nutr.* 31:S116–S122 (1978).

Finegold et al., "Fecal microbial flora in Seventh Day Adventist populations and control subjects," *Am. J. Clin. Nutr.* 30:1781–1792 (1977).

Gilleland et al., "Use of synthetic peptides to identify surface–exposed, linear B–cell epitopes within outer membrane protein F of *Pseudomonas aeruginosa*," *Curr. Microbiol.* 31:279–86 (1995).

Gionchetti et al., "Review—antibiotic treatment in inflammatory bowel disease: rifaximin, a new possible approach," *Eur. Rev. Med. Pharmacol. Sci.* 3:27–30 (1999).

Graham et al., "DNA hybridization studies on the association of *Pseudomonas maltophilia* with inflammatory bowel diseases," *J. Lab. Clin. Med.* 101:940–954 (1983).

Gui et al., "Two–year–outcomes analysis of Crohn's disease treated with rifabutin and macrolide antibiotics," *J. Antimicrob. Chemother.* 39:393–400 (1997).

Ichikawa et al., "Interaction of *Pseudomonas aeruginosa* with epithelial cells: Identification of differentially regulated genes by expression microarray analysis of human cDNAs," *Proc. Natl. Acad. Sci. USA* 97:9659–9664 (2000).

Jang et al., "Human immune response to a *Pseudomonas aeruginosa* outer membrane protein vaccine," *Vaccine* 17:158–68 (1999).

Janowitz et al., "The role of the fecal stream in Crohn's disease: An historical and analytic review," *Inflamm. Bowel Dis.* 4:29–39 (1998).

Ji et al., "Identification of Critical Staphylococcal Genes Using Conditional Phenotypes Generated by Antisense RNA," *Science* 293:2266–2269 (2001).

Juliano and Yoo, "Aspects of the transport and delivery of antisense oligonucleotides," *Curr. Opin. Mol. Ther.* 2:297–303 (2000).

Knapp et al., "A recombinant hybrid outer membrane protein for vaccination against *Pseudomonas aeruginosa*," *Vaccine* 17:1663–1666 (1999).

Koukalova et al., "Development of a vaccine for treatment of urinary tract inflammatory diseases," *Bratisl. Lek. Listy* 100:92–5 (1999).

Lang et al., "Effect of high–affinity anti–*Pseudomonas aeruginosa* lipopolysaccharide antibodies induced by immunization on the rate of *Pseudomonas aeruginosa* infection in patients with cystic fibrosis," *J. Pediatr.* 127:711–717 (1995).

Langholz et al., "Treatment of Crohn's disease with fusidic acid: An antibiotic with immunosuppressive properties similar to cyclosporin," *Aliment Pharmacol. Ther.* 6:495–502 (1992).

Lee et al., "Conformation–dependent antibody response to *Pseudomonas aeruginosa* outer membrane proteins induced by immunization in humans," *FEMS Immunol. Med. Microbiol.* 27:79–85 (2000).

Lee et al., "Immunization of burn–patients with a *Pseudomonas aeruginosa* outer membrane protein vaccine elicits antibodies with protective efficacy," *Vaccine* 18:1952–61 (2000).

Leoni et al., "Functional analysis of PvdS, an iron starvation sigma factor of *Pseudomonas aeruginosa*," *J. Bacteriol.* 182:1481–1491 (2000).

Lewin and Hauswirth, "Ribozyme gene therapy: Applications for molecular medicine," *Trends. Mol. Med.* 7:221–228 (2001).

Li et al., "The structural basis of T cell activation by superantigens," *Annu. Rev. Immunol.* 17:435–466 (1999).

Lister et al., "β–lactamase inhibitor combinations with extended–spectrum penicillins: Factors influencing antibacterial activity against enterobacteriaceae and *Pseudomonas aeruginosa*," *Pharmacotherapy* 20:213S–218S (2000).

Mansouri et al., "Safety and immunogenicity of a *Pseudomonas aeruginosa* hybrid outer membrane protein F–I vaccine in human volunteers," *Infect. Immun.* 67:1461–70 (1999).

Marrack and Kappler, "Subversion of the immune system by pathogens," *Cell* 76:323–332 (1994).

Martin and Rohodes, "Bacteria and inflammatory bowel disease," *Curr. Opin. Infect. Dis.* 13:503–509 (2000).

Moss et al., "Polymerase chain reaction detection of *Mycobacterium paratuberculosis* and *Mycobacterium avium* subsp *silvaticum* in long term cultures from Crohn's disease and control tissues," *Gut* 33:1209–1213 (1992).

Parent and Mitchell, "Cell wall–defective variants of Pseudomonas–like (group Va) bacteria in Crohn's disease," *Gastroenterology* 75:368–372 (1978).

Parent and Mitchell, "Bacterial variants: Etiologic agent in Crohn's disease?," *Gastroenterology* 71:365–368 (1976).

Park et al., "General pharmacology of a Pseudomonas vaccine prepared from outer–membrane fractions of *Pseudomonas aeruginosa*," *Arzne–Forsch/Drug Res.* 46(II):1001–6 (1996).

Podolsky, "Lessons from genetic models of inflammatory bowel disease," *Acta Gastro–Enterol. Belg.* 60:163–165 (1997).

Powrie et al., "Inhibition of Th1 Responses Prevents Inflammatory Bowel Disease in scid Mice Reconstituted with $CD45RB^{hi}$ $CD4^+$ T Cells," *Immunity* 1:553–562 (1994).

Prantera et al., "Antimycobacterial therapy in Crohn's disease: Results of a controlled, double–blind trial with a multiple antibiotic regime," *Am. J. Gastroenterol.* 89:513–518 (1994).

Prantera et al., "An Antibiotic Regimen for the Treatment of Active Crohn's Disease: A Randomized, controlled Clinical Trial of Metronidazole plus Ciprofloxacin," *Am. J. Gastroenterol.* 91:328–332 (1996).

Rawling and Martin, "Epitope mapping of the *Pseudomonas aeruginosa* major outer membrane porin protein OprF," *Infect. Immun.* 63:38–42 (1995).

Sanderson et al., "*Mycobacterium paratuberculosis* DNA in Crohn's disease tissue," *Gut* 33:890–896 (1992).

Seibold et al., "pANCA Represents a Cross–Reactivity to Enteric Bacterial Antigens," *Journal of Clinical Immunology* 18:153–160 (1998).

Sendid et al., "Specific antibody response to oligomannosidic epitopes in Crohn's disease," *Clin. Diag. Lab. Immunol.* 3:219–226 (1996).

Sexton et al., "Transcriptional regulation of the iron–responsive sigma factor gene *pbrA*," *Mol. Gen. Genet.* 250:50–58 (1996).

Sexton et al., "Iron–responsive gene expression in *Pseudomonas fluorescens* M114: cloning and characterization of a transcription–activating factor, PbrA," *Mol. Microbiol.* 15:297–306 (1995).

Sheth et al., "Development of an anti–adhesive vaccine for *Pseudomonas aeruginosa* targeting the C–terminal region of the pilin structural protein," *Biomed. Pept. Proteins Nucleic Acids* 1:141–8 (1995).

Siegel et al., "Parathyroid hormone stimulates dephosphorylation of the renoredoxin component of the 25–hydroxyvitamin $D_3$–1α–hydroxylase from rat renal cortex," *J. Biol. Chem.* 261:16998–17003 (1986).

Sonnenberg, "Occupational distribution of inflammatory bowel disease among German employees," *Gut* 31:1037–1040 (1990).

Stanislavsky et al., "Antigenic and Protective Properties of Lipopolysaccharides of R–Forms of some grame–negative bacteria," *Zh. Mikrobiol. Epidemiol. Immunobiol.* 52–56 (1998).

Stanislavsky and Lam, "*Pseudomonas aeruginosa* antigens as potential vaccines," *FEMS Microbiol. Rev.* 21:243–77 (1997).

Stanislavsky et al., "R–form lipopolysaccharides (LPS) of Gram–negative bacteria as possible vaccine antigens," *FEMS Immunol. Med. Microbiol.* 18:139–45 (1997).

Stover et al., "Complete genome sequence of *Pseudomonas aeruginosa* PA01, an opportunistic pathogen," *Nature* 406:959–964 (2000).

Sutton et al., "Identification of a Novel Bacterial Sequence Associated with Crohn's Disease," *Gastroenterology* 119:23–31 (2000).

Thomas et al., "Controlled trial of antituberculosis chemotherapy in Crohn's disease: A five year follow up study," *Gut* 42:497–500 (1998).

Vannuffel et al., "Occurrence, in Crohn's Disease, of Antibodies Directed against a Species–Specific Recombinant Polypeptide of *Mycobacterium paratuberculosis*," *Clinical and Diagnostic Laboratory Immunology* 1:241–243 (1994).

von Specht et al., "Outer membrane proteins of *Pseudomonas aeruginosa* as vaccine candidates," *J. Biotechnol.* 44:145–53 (1996).

von Specht, "A new vaccine against *P. aeruginosa* infections. Based on recombinant *P. aeruginosa* outer membrane proteins," *Zentralb. Chir.* 124:298–302 (1999).

Wang et al., "Overexpression of murine fizzy–related (fzr) increases natural killer cell–mediated cell death and suppresses tumor growth," *Blood* 96:259–263 (2000).

Wayne et al., "Immunoglobulin A (IgA) and IgG Serum Antibodies to Mycobacterial Antigens in Crohn's Disease Patients and Their Relatives," *J. Clin. Microbiology* 30:2013–2018 (1992).

Weiner et al., "Oral Tolerance: Immunologic Mechanisms and Treatment of Animal and Human Organ–Specific Autoimmune Diseases by Oral Administration of Autoantigens," *Ann. Rev. Immunol.* 12:809–837 (1994).

Weiner, "Oral Tolerance: Mobilizing the Gut," *Hospital Practice* Sep. 15th, pp. 53–58 (1995).

Wilson et al., "Phylogenetic placement of community members of human colonic biota," *Clin. Infect. Dis.* 25(S2):S114–S116 (1997).

Wilson et al., "Analysis of promoters recognized by PvdS, an extracytoplasmic–function sigma factor protein from *Pseudomonas aeruginosa*," *J. Bacteriol.* 183:2151–2155 (2001).

Xiong et al., "The oxygen–and iron–dependent sigma factor *pvdS* of *Pseudomonas aeruginosa* is an important virulence factor in experimental infective endocarditis," *J. Infect. Dis.* 181:1020–1026 (2000).

Yamaguchi et al., "Activities of antimicrobial agents against 5,180 clinical isolates obtained from 26 medical institutions during 1998 in Japan. Levofloxacin–Surveillance Group," *Japanese J. Antibiot.* 53:387–408 (1998).

* cited by examiner

```
atgacggaaccagtatccacaggcaggtgcgattcacccttctccaggcgttcgtcgacaatcg
actgattctggtgaagatcgcggcccgtatcaccgggtgccgctcccgcgccgaagacgtggtgc
aggacgcctacttccggctgcagtcggcgccgaccatcacctcatcgttcaaggcccaactgagt
tatctgtttcagatcgtacgcaacctggcgatcgatcattaccgcaagcaggccctggagctcaa
atactccgggaccgaagaggaaggcttgaatgtggttattcacggcgcttcaccggaaacctcgc
acatcaatttcacaccctggaaaacatcgccgacgccctgacgcaactgccccagcgcacccgc
tacgcgttcgagatgtaccgcttgcatggcgtgccgcaaaaagacatcgccaaggagcttggggt
gtctccgaccttggtgaacttcatgattcgcgatgcgctggtgcattgccgcaaggtgtcgggca
gtcatagcgatacgtttgcgcggcgggtttaa
```

FIGURE 4A

```
MTEPVSTGRCDSPLLQAFVDNRLILVKIAARITGCRSRAEDVVQDAYFRLQSAPTITSSFKAQLS
YLFQIVRNLAIDHYRKQALELKYSGTEEEGLNVVIHGASPETSHINFNTLENIADALTQLPQRTR
YAFEMYRLHGVPQKDIAKELGVSPTLVNFMIRDALVHCRKVSGSHSDTFARRV
```

FIGURE 4B

ATGCGCACCATGGTCGACAGTGGCCAATTGACCGACCCCGAGAGCGCCCGCGGCAAGTTGCTGCA
AACCGCGGCTCATCTGTTTCGCAACAAGGGTTTCGAGCGCACCACCGTGCGAGATCTGGCCAGCG
CCGTGGGCATCCAGTCCGGCAGCATCTTTCATCACTTCAAGAGCAAGGATGAGATATTGCGTGCC
GTGATGGAGGAAACCACCCATTACAACACCGCGATGATGCGCGCTTCACTGGAAGAAGCGAGCAC
GGTGCGCGAACGCGTGCTGGCGCTGATCCGCTGCAAGTTGCAGTCGATCATGGGCGGCAGTGGCG
AGGCCATGGCGGTGCTGGTCTACGAATGGCGCTCGCTGTCGGCCGAAGGCCAGGCGCACGTGCTG
GCCCTGCGTGACGTGTATGAGCAGATCTGGTTGCAGGTACTGGGCGAGGCCAAGGCCGCTGGCTA
CATCCGGGGCGACGTGTTTATTACCCGGCGCTTCCTCACCGGGGCCTTATCCTGGACCACCACCt
GGTTTCGTGCCCAAGGCAGCC*TGACCCTTGAGGAGTTGGCCGAAGA*GGCCttgttgaTggtGCTG
AAGTCGGACTGA

FIGURE 5A

MRTMVDSGQLTDPESARGKLLQTAAHLFRNKGFERTTVR<u>DLASAVGIQSGSIFHHFKSK̇DEILRA
VMEETTHYNTAMMRASLEEASTVRERVLALIRCKLQSIMGGSGEAMA</u>VLVYEWRSLSAEGQAHVL
ALRDVYEQIWLQVLGEAKAAGYIRGDVFITRRFLTGALSWTTTWFRAQGSLTLEELAEEALLMVL
KSD

FIGURE 5B

```
   1 cgacggcccg ggctggtctg tttgagttga gggtgcaggt catcgccgag caacacggcg
  61 attttcagcg ggatgtgcgc gttatcgcag gccgcttgca gggcggcggc gcaggcttgg
 121 gggttgatac caccggcatt gctgatcacc cggatgccct ggcgctggat atccgccagc
 181 aggggtgtca gcacctcgac aaaatccgtg gcgtaaccgg ccttggggtc tttcaggcgg
 241 gcaccggcga ggatcgacag ggtgacttcc gcgaggtaat cgaacaccag gtaatccaag
 301 gcaccgccct gcaccaattg ggcggcggcg gtgcaagtgt cgccccagaa ggcgctggcg
 361 cagccgatac gtaccgtctt gctcatgaga aatccttcct ccaagggctg gtgccgagac
 421 taccaagcaa gcgcttggtt tgtaaactcc agtcacaagt tttacccaag cgcttgcttg
 481 ggtggcagtc acggcctaaa ttgccggcca agacgacagt agacgtgaag gagagcagca
 541 tggatgagca caaagccctg ggggtgatgc gcaccatggt cgacagtggc caattgaccg
 601 accccgagag cgcccgcggc aagttgctgc aaaccgcggc tcatctgttt cgcaacaagg
 661 gtttcgagcg caccaccgtg cgagatctgg ccagcgccgt gggcatccag tccggcagca
 721 tctttcatca cttcaagagc aaggatgaga tattgcgtgc cgtgatggag gaaaccaccc
 781 attacaacac cgcgatgatg cgcgcttcac tggaagaagc gagcacggtg cgcgaacgcg
 841 tgctggcgct gatccgctgc aagttgcagt cgatcatggg cggcagtggc gaggccatgg
 901 cggtgctggt ctacgaatgg cgctcgctgt cggccgaagg ccaggcgcac gtgctggccc
 961 tgcgtgacgt gtatgagcag atctggttgc aggtactggg cgaggccaag gccgctggct
1021 acatccgggg cgacgtgttt attacccggc gcttcctcac cggggcctta tcctggacca
1081 ccacctggtt tcgtgcccaa ggcagcctga cccttgagga gttggccgaa gaggccttgt
1141 tgatggtgct gaagtcggac tgaggcgcaa gttattaatt tgctgcgaa agttgtctcc
1201 cccaataaaa acgcctagct tatcggcatt gaactcttca acggtgtgtg cctcgatgtt
1261 ttcgccatgg cggctggctg caggacttac tttatgggca ctgggcaccg ccgcgtggac
1321 gcaggctggt gccgcgcagt tggtgagaat cggcgcggcg cattttccgc cctacaccgt
1381 acgccctgaa caaggcgccg acaccgggtt gctgccgcaa ttggtcgagg cgttgaacgc
1441 tgcgcaaacc gattaccagt ttgtggtggt gcctacctcg atacctcggc gttttcgtga
1501 cttcgagcaa ggccgggtcg acatggcgat cttcgaaaac ccgtcctggg gttggcagaa
1561 tattgcccat accagtgttg atatgggggct gaagatgcgg agattttttgt cgctcagcgt
1621 cagcccggtc gcgaccagag ttatttttcc gacctcaccg gaagcgctgg cggtattcag
1681 cgggtatcac tatgcctttg ctgacttcaa tcccgatccc aagaacatgc cgagcgtttc
1741 aacgcgacgt tgacctactc ccatgacagt aatctgctga tggttgctcg tgggcgtgca
1801 gatattgcgc tggttacccg ctcgtacctg agtgatttca tggtgcgcaa cgcggacatg
1861 gcggggcagt ttttggtgtc ggagcgtatt gaccaggtgt atcaccacta cgcgttgttg
1921 cgnccaaggc acccgatcac tggtccggcg tttgccggaa ctgctcaagt cttgcgcgac
1981 agtggccaga tgctgaagat ttttgagccg tatcgtattg atgtgacgcc ggtgccctaa
2041 ggtcttagta agtaaaatcc ttcgggctca gtgggatcaa ctgtggaagc tggcttgcct
2101 gcgatggcgg cctgacagcc gacacagatt aattgatgct gatgccccgc gatccaatgt
2161 gggagcttgg cttgcctgcg aagacggcct gacagtcaac acagttggac cgtgtacata
2221 tccatccctt gcggtaaccgg gctacttagg gttccgcttt tacagcggct cacttttgaa
2281 aagcgcaaaa gtaagcaaaa cgctcttgcc ccaccactcg gcacctcgcc aggctcggtg
2341 tgcccgtaat ccgccagtga tttgggggggc gcccacgcg catccatgcg cggggcggct
2401 aaacggatcc ctgccggttt accccccaaa tccctgtcg aattccggcc agcgtggttt
2461 aacggggcgc ctaagatcaa aagccagatc aagatcacaa gcagatcaag atcacaagca
2521 gatcaagatc acaagcagat caagatcaca agcagatcaa gatcaagagc gggctcgctt
2581 cgcatcgtag tttccgtgga gcccttaccc acatatgtcg gcgctggatt aaacccgccg
2641 cgcaaacgta tcgctatgac tgcccgacac cttgcggcaa tgcaccagcg catcgcgaat
2701 catgaagttc accaaggtcg gagacacccc aagctccttg gcgatgtctt tttcggcac
2761 gccatgcaag cggtacatct cgaacgcgta gcgggtgcgc tggggcagtt gcgtcagggc
2821 gtcggcgatg ttttccaggg tgttgaaatt gatgtgcgag gtttccggtg aagcgccgtg
2881 aataaccaca ttcaagcctt cctcttcggt cccggagtat ttgagctcca gggcctgctt
2941 gcggtaatga tcgatcgcca ggttgcgtac gatctgaaac agataactca gttgggcctt
3001 gaacgatgag gtgatggtcg gcgccgactg cagccggaag taggcgtcct gcaccacgtc
3061 ttcggcgcgg gagcggcacc cggtgatacg gccgcgatc ttcaccagaa tcagtcgatt
3121 gtcgacgaac gcctggagaa ggggtgaatc gcacctgcct gtggatactg gttccgtcat
```

FIGURE 6 (page 1 of 2)

```
3181 ggaaatcacc ttgctgcgaa taggttaggg aagggcatcc ctgttaggcc tcctacatat
3241 cgggcaccaa attatgctta atgataatga ttgtcaaatg agaaggcgaa ctaatcttat
3301 gccttggcga aggtgtgaac cacgtctcgc tccccccgg cgactaatta tttgaaggct
3361 ccgtccgttc tcatgggtga caggttcgtt agtacaacgg ccaaggacca gcacccgcag
3421 gaggaccaga tgggttttta tcgtgcattc agcgtgtttc agttcggagt cctcgcggga
3481 tgagtacgtc cctgcggctg cgcctgtttt gcctgcccca ctcaggcgcc agcgcctcgg
3541 tctacgctcg ctggcgcggg gtgctgccgg actggctgca agtgtgcccg ctggaattgc
3601 cgggacgcgg catgcgcatg gacgagccat tgcagcgcga taccagcccg ggccgtc
```

FIGURE 6 (page 2 of 2)

SEQUENCE LISTING

```
<160> NUMBER OF SEQ ID NOS: 10

<210> SEQ ID NO 1
<211> LENGTH: 551
<212> TYPE: DNA
<213> ORGANISM: P. fluorescens
<220> FEATURE:
<221> NAME/KEY: CDS
<222> LOCATION: (1)...(549)

<400> SEQUENCE: 1
```

```
atg acg gaa cca gta tcc aca ggc agg tgc gat tca ccc ctt ctc cag    48
Met Thr Glu Pro Val Ser Thr Gly Arg Cys Asp Ser Pro Leu Leu Gln
 1               5                  10                  15 gcg ttc gtc gac aat cga ctg att ctg gtg aag atc gcg gcc cgt atc    96
Ala Phe Val Asp Asn Arg Leu Ile Leu Val Lys Ile Ala Ala Arg Ile
             20                  25                  30 acc ggg tgc cgc tcc cgc gcc gaa gac gtg gtg cag gac gcc tac ttc   144
Thr Gly Cys Arg Ser Arg Ala Glu Asp Val Val Gln Asp Ala Tyr Phe
         35                  40                  45 cgg ctg cag tcg gcg ccg acc atc acc tca tcg ttc aag gcc caa ctg   192
Arg Leu Gln Ser Ala Pro Thr Ile Thr Ser Ser Phe Lys Ala Gln Leu
     50                  55                  60 agt tat ctg ttt cag atc gta cgc aac ctg gcg atc gat cat tac cgc   240
Ser Tyr Leu Phe Gln Ile Val Arg Asn Leu Ala Ile Asp His Tyr Arg
 65                  70                  75                  80 aag cag gcc ctg gag ctc aaa tac tcc ggg acc gaa gag gaa ggc ttg   288
Lys Gln Ala Leu Glu Leu Lys Tyr Ser Gly Thr Glu Glu Glu Gly Leu
                 85                  90                  95 aat gtg gtt att cac ggc gct tca ccg gaa acc tcg cac atc aat ttc   336
Asn Val Val Ile His Gly Ala Ser Pro Glu Thr Ser His Ile Asn Phe
             100                 105                 110 aac acc ctg gaa aac atc gcc gac gcc ctg acg caa ctg ccc cag cgc   384
Asn Thr Leu Glu Asn Ile Ala Asp Ala Leu Thr Gln Leu Pro Gln Arg
         115                 120                 125 acc cgc tac gcg ttc gag atg tac cgc ttg cat ggc gtg ccg caa aaa   432
Thr Arg Tyr Ala Phe Glu Met Tyr Arg Leu His Gly Val Pro Gln Lys
     130                 135                 140 gac atc gcc aag gag ctt ggg gtg tct ccg acc ttg gtg aac ttc atg   480
Asp Ile Ala Lys Glu Leu Gly Val Ser Pro Thr Leu Val Asn Phe Met
145                 150                 155                 160 att cgc gat gcg ctg gtg cat tgc cgc aag gtg tcg ggc agt cat agc   528
Ile Arg Asp Ala Leu Val His Cys Arg Lys Val Ser Gly Ser His Ser
                 165                 170                 175 gat acg ttt gcg cgg cgg gtt ta                                    551
Asp Thr Phe Ala Arg Arg Val
             180
```

<210> SEQ ID NO 2
<211> LENGTH: 183
<212> TYPE: PRT
<213> ORGANISM: P. fluorescens

<400> SEQUENCE: 2

```
Met Thr Glu Pro Val Ser Thr Gly Arg Cys Asp Ser Pro Leu Leu Gln
 1               5                  10                  15

Ala Phe Val Asp Asn Arg Leu Ile Leu Val Lys Ile Ala Ala Arg Ile
             20                  25                  30

Thr Gly Cys Arg Ser Arg Ala Glu Asp Val Val Gln Asp Ala Tyr Phe
         35                  40                  45

Arg Leu Gln Ser Ala Pro Thr Ile Thr Ser Ser Phe Lys Ala Gln Leu
     50                  55                  60

Ser Tyr Leu Phe Gln Ile Val Arg Asn Leu Ala Ile Asp His Tyr Arg
 65                  70                  75                  80

Lys Gln Ala Leu Glu Leu Lys Tyr Ser Gly Thr Glu Glu Glu Gly Leu
                 85                  90                  95

Asn Val Val Ile His Gly Ala Ser Pro Glu Thr Ser His Ile Asn Phe
             100                 105                 110

Asn Thr Leu Glu Asn Ile Ala Asp Ala Leu Thr Gln Leu Pro Gln Arg
         115                 120                 125
```

```
Thr Arg Tyr Ala Phe Glu Met Tyr Arg Leu His Gly Val Pro Gln Lys
            130                 135                 140

Asp Ile Ala Lys Glu Leu Gly Val Ser Pro Thr Leu Val Asn Phe Met
145                 150                 155                 160

Ile Arg Asp Ala Leu Val His Cys Arg Lys Val Ser Gly Ser His Ser
                165                 170                 175

Asp Thr Phe Ala Arg Arg Val
            180

<210> SEQ ID NO 3
<211> LENGTH: 184
<212> TYPE: PRT
<213> ORGANISM: P. fluorescens

<400> SEQUENCE: 3

Met Thr Glu Gln Val Ser Thr Ser Lys Cys Asp Ser Pro Leu Leu His
  1               5                  10                  15

Ala Phe Val Asp Asn Arg Leu Ile Leu Val Lys Ile Ala Ala Arg Ile
                 20                  25                  30

Thr Gly Cys Arg Ser Thr Ala Glu Asp Val Val Gln Asp Ala Phe Phe
             35                  40                  45

Arg Leu Gln Ser Ala Pro Pro Ile Thr Ser Ser Ile Lys Ala Gln Leu
 50                  55                  60

Ser Tyr Leu Phe Gln Ile Val Arg Asn Leu Ala Ile Asp His Tyr Arg
 65                  70                  75                  80

Lys Gln Ala Leu Glu Gln Lys Tyr Ser Gly Pro Glu Glu Gly Leu
                 85                  90                  95

Asn Val Val Ile Gln Gly Ala Ser Pro Glu Thr Ser His Ile Asn Phe
                100                 105                 110

Ser Thr Leu Glu Asn Ile Ala Asp Ala Leu Thr Glu Leu Pro Ser Arg
            115                 120                 125

Thr Arg Tyr Ala Phe Glu Met Tyr Arg Leu His Gly Val Pro Gln Lys
            130                 135                 140

Asp Ile Ala Lys Glu Leu Gly Val Ser Pro Thr Leu Val Asn Phe Met
145                 150                 155                 160

Ile Arg Asp Ala Leu Val His Cys Arg Lys Val Ser Gly Ser Arg Arg
                165                 170                 175

Asp Ala Val Ala Val Gly Arg Arg
            180

<210> SEQ ID NO 4
<211> LENGTH: 597
<212> TYPE: DNA
<213> ORGANISM: P. fluorescens
<220> FEATURE:
<221> NAME/KEY: CDS
<222> LOCATION: (1)...(594)

<400> SEQUENCE: 4 atg cgc acc atg gtc gac agt ggc caa ttg acc gac ccc gag agc gcc      48
Met Arg Thr Met Val Asp Ser Gly Gln Leu Thr Asp Pro Glu Ser Ala
  1               5                  10                  15 cgc ggc aag ttg ctg caa acc gcg gct cat ctg ttt cgc aac aag ggt      96
Arg Gly Lys Leu Leu Gln Thr Ala Ala His Leu Phe Arg Asn Lys Gly
                 20                  25                  30 ttc gag cgc acc acc gtg cga gat ctg gcc agc gcc gtg ggc atc cag     144
Phe Glu Arg Thr Thr Val Arg Asp Leu Ala Ser Ala Val Gly Ile Gln
             35                  40                  45
```

-continued

```
tcc ggc agc atc ttt cat cac ttc aag agc aag gat gag ata ttg cgt    192
Ser Gly Ser Ile Phe His His Phe Lys Ser Lys Asp Glu Ile Leu Arg
    50                  55                  60 gcc gtg atg gag gaa acc acc cat tac aac acc gcg atg atg cgc gct    240
Ala Val Met Glu Glu Thr Thr His Tyr Asn Thr Ala Met Met Arg Ala
 65                  70                  75                  80 tca ctg gaa gaa gcg agc acg gtg cgc gaa cgc gtg ctg gcg ctg atc    288
Ser Leu Glu Glu Ala Ser Thr Val Arg Glu Arg Val Leu Ala Leu Ile
                 85                  90                  95 cgc tgc aag ttg cag tcg atc atg ggc ggc agt ggc gag gcc atg gcg    336
Arg Cys Lys Leu Gln Ser Ile Met Gly Gly Ser Gly Glu Ala Met Ala
            100                 105                 110 gtg ctg gtc tac gaa tgg cgc tcg ctg tcg gcc gaa ggc cag gcg cac    384
Val Leu Val Tyr Glu Trp Arg Ser Leu Ser Ala Glu Gly Gln Ala His
        115                 120                 125 gtg ctg gcc ctg cgt gac gtg tat gag cag atc tgg ttg cag gta ctg    432
Val Leu Ala Leu Arg Asp Val Tyr Glu Gln Ile Trp Leu Gln Val Leu
    130                 135                 140 ggc gag gcc aag gcc gct ggc tac atc cgg ggc gac gtg ttt att acc    480
Gly Glu Ala Lys Ala Ala Gly Tyr Ile Arg Gly Asp Val Phe Ile Thr
145                 150                 155                 160 cgg cgc ttc ctc acc ggg gcc tta tcc tgg acc acc acc tgg ttt cgt    528
Arg Arg Phe Leu Thr Gly Ala Leu Ser Trp Thr Thr Thr Trp Phe Arg
                165                 170                 175 gcc caa ggc agc ctg acc ctt gag gag ttg gcc gaa gag gcc ttg ttg    576
Ala Gln Gly Ser Leu Thr Leu Glu Glu Leu Ala Glu Glu Ala Leu Leu
            180                 185                 190 atg gtg ctg aag tcg gac tga                                         597
Met Val Leu Lys Ser Asp
        195
```

<210> SEQ ID NO 5
<211> LENGTH: 198
<212> TYPE: PRT
<213> ORGANISM: P. fluorescens

<400> SEQUENCE: 5

```
Met Arg Thr Met Val Asp Ser Gly Gln Leu Thr Asp Pro Glu Ser Ala
 1               5                  10                  15

Arg Gly Lys Leu Leu Gln Thr Ala Ala His Leu Phe Arg Asn Lys Gly
            20                  25                  30

Phe Glu Arg Thr Thr Val Arg Asp Leu Ala Ser Ala Val Gly Ile Gln
        35                  40                  45

Ser Gly Ser Ile Phe His His Phe Lys Ser Lys Asp Glu Ile Leu Arg
    50                  55                  60

Ala Val Met Glu Glu Thr Thr His Tyr Asn Thr Ala Met Met Arg Ala
 65                  70                  75                  80

Ser Leu Glu Glu Ala Ser Thr Val Arg Glu Arg Val Leu Ala Leu Ile
                 85                  90                  95

Arg Cys Lys Leu Gln Ser Ile Met Gly Gly Ser Gly Glu Ala Met Ala
            100                 105                 110

Val Leu Val Tyr Glu Trp Arg Ser Leu Ser Ala Glu Gly Gln Ala His
        115                 120                 125

Val Leu Ala Leu Arg Asp Val Tyr Glu Gln Ile Trp Leu Gln Val Leu
    130                 135                 140

Gly Glu Ala Lys Ala Ala Gly Tyr Ile Arg Gly Asp Val Phe Ile Thr
145                 150                 155                 160

Arg Arg Phe Leu Thr Gly Ala Leu Ser Trp Thr Thr Thr Trp Phe Arg
```

-continued

```
                165                 170                 175

Ala Gln Gly Ser Leu Thr Leu Glu Glu Leu Ala Glu Glu Ala Leu Leu
            180                 185                 190

Met Val Leu Lys Ser Asp
        195

<210> SEQ ID NO 6
<211> LENGTH: 17
<212> TYPE: DNA
<213> ORGANISM: P. fluorescens

<400> SEQUENCE: 6
agatcaagat cacaagc                                                  17

<210> SEQ ID NO 7
<211> LENGTH: 187
<212> TYPE: PRT
<213> ORGANISM: P. aeruginosa

<400> SEQUENCE: 7

Met Ser Glu Gln Leu Ser Thr Arg Arg Cys Asp Thr Pro Leu Leu Gln
 1               5                  10                  15

Ala Phe Val Asp Asn Arg Thr Ile Leu Val Lys Ile Ala Ala Arg Ile
            20                  25                  30

Thr Gly Cys Arg Ser Arg Ala Glu Asp Val Val Gln Asp Ala Phe Phe
        35                  40                  45

Arg Leu Gln Ser Ala Pro Gln Ile Thr Ser Ser Glu Lys Ala Gln Leu
    50                  55                  60

Ser Tyr Leu Phe Gln Ile Val Arg Asn Leu Ala Ile Asp His Tyr Arg
65                  70                  75                  80

Lys Gln Ala Leu Glu Gln Lys Tyr Ser Gly Pro Glu Glu Gly Leu
                85                  90                  95

Asn Val Val Ile Gln Gly Ala Ser Pro Glu Thr Ser His Ile Asn Tyr
            100                 105                 110

Ala Thr Leu Glu His Ile Ala Asp Ala Leu Thr Glu Leu Pro Lys Arg
        115                 120                 125

Thr Arg Tyr Ala Phe Glu Met Tyr Arg Leu His Gly Val Pro Gln Lys
    130                 135                 140

Asp Ile Ala Lys Glu Leu Gly Val Ser Pro Thr Leu Val Asn Phe Met
145                 150                 155                 160

Ile Arg Asp Ala Leu Val His Cys Arg Lys Val Thr Ala Glu Arg Gln
                165                 170                 175

Gly Asp Asn Val Thr His Leu Ser Ala Arg Arg
            180                 185

<210> SEQ ID NO 8
<211> LENGTH: 176
<212> TYPE: PRT
<213> ORGANISM: P. putida

<400> SEQUENCE: 8

Met Ala Glu Gln Leu Ser Thr Ser Lys Cys Asp Ser Pro Leu Leu Gln
 1               5                  10                  15

Ala Phe Val Asp Asn Arg Ser Ile Leu Val Lys Ile Ala Ala Arg Ile
            20                  25                  30

Thr Gly Cys Arg Ser Arg Ala Glu Asp Val Val Gln Asp Ala Phe Phe
        35                  40                  45
```

```
Arg Leu Ser Ala Ala Pro Gln Ile Thr Ser Ser Phe Lys Ala Gln Leu
        50                  55                  60

Ser Tyr Leu Phe Gln Ile Val Arg Asn Leu Ala Ile Asp His Tyr Arg
 65                  70                  75                  80

Lys Gln Ala Met Glu Leu Lys Tyr Ser Gly Ser Glu Glu Glu Gly Leu
                85                  90                  95

Asn Val Val Ile Gln Asn Ala Ser Pro Glu Ala Thr His Ile Asn Leu
               100                 105                 110

Ala Ala Leu Asp Glu Ile Ala Glu Ala Leu Asn Glu Leu Pro Gln Arg
               115                 120                 125

Thr Arg Ser Ala Phe Glu Met Tyr Arg Leu His Gly Val Pro Gln Lys
       130                 135                 140

Asp Ile Ala Lys Glu Leu Gly Val Ser Pro Thr Leu Val Asn Phe Met
145                 150                 155                 160

Ile Arg Asp Ala Leu Val His Ser Ala Lys Thr Ala Asn Arg Gln Val
               165                 170                 175

<210> SEQ ID NO 9
<211> LENGTH: 160
<212> TYPE: PRT
<213> ORGANISM: Artificial Sequence
<220> FEATURE:
<223> OTHER INFORMATION: synthetic consenusus sequence

<400> SEQUENCE: 9

Met Glu Gln Ser Thr Cys Asp Ser Pro Leu Leu Gln Ala Phe Val Asp
  1               5                  10                  15

Asn Arg Ile Leu Val Lys Ile Ala Ala Arg Ile Thr Gly Cys Arg Ser
                 20                  25                  30

Arg Ala Glu Asp Val Val Gln Asp Ala Phe Phe Arg Leu Gln Ser Ala
             35                  40                  45

Pro Ile Thr Ser Ser Phe Lys Ala Gln Leu Ser Tyr Leu Phe Gln Ile
         50                  55                  60

Val Arg Asn Leu Ala Ile Asp His Tyr Arg Lys Gln Ala Leu Glu Lys
 65                  70                  75                  80

Tyr Ser Gly Glu Glu Glu Gly Leu Asn Val Val Ile Gln Gly Ala Ser
                85                  90                  95

Pro Glu Thr Ser His Ile Asn Thr Leu Glu Ile Ala Asp Ala Leu Thr
               100                 105                 110

Glu Leu Pro Arg Thr Arg Tyr Ala Phe Glu Met Tyr Arg Leu His Gly
           115                 120                 125

Val Pro Gln Lys Asp Ile Ala Lys Glu Leu Gly Val Ser Pro Thr Leu
       130                 135                 140

Val Asn Phe Met Ile Arg Asp Ala Leu Val His Cys Arg Lys Val Arg
145                 150                 155                 160

<210> SEQ ID NO 10
<211> LENGTH: 3657
<212> TYPE: DNA
<213> ORGANISM: P. fluorescens
<220> FEATURE:
<221> NAME/KEY: misc_feature
<222> LOCATION: 1923
<223> OTHER INFORMATION: n = A,T,C or G

<400> SEQUENCE: 10
cgacggcccg ggctggtctg tttgagttga gggtgcaggt catcgccgag caacacggcg    60 atttcagcg ggatgtgcgc gttatcgcag gccgcttgca gggcggcggc gcaggcttgg   120
```

```
gggttgatac caccggcatt gctgatcacc cggatgccct ggcgctggat atccgccagc     180
aggggtgtca gcacctcgac aaaatccgtg gcgtaaccgg ccttgggggtc tttcaggcgg    240
gcaccggcga ggatcgacag ggtgacttcc gcgaggtaat cgaacaccag gtaatccaag     300
gcaccgccct gcaccaattg ggcggcggcg gtgcaagtgt cgccccagaa ggcgctggcg     360
cagccgatac gtaccgtctt gctcatgaga atccttcct ccaagggctg gtgccgagac      420
taccaagcaa gcgcttggtt tgtaaactcc agtcacaagt tttacccaag cgcttgcttg     480
ggtggcagtc acggcctaaa ttgccggcca agacgacagt agacgtgaag gagagcagca    540
tggatgagca caaagccctg ggggtgatgc gcaccatggt cgacagtggc caattgaccg    600
accccgagag cgcccgcggc aagttgctgc aaaccgcggc tcatctgttt cgcaacaagg   660
gtttcgagcg caccaccgtg cgagatctgg ccagcgccgt gggcatccag tccggcagca    720
tctttcatca cttcaagagc aaggatgaga tattgcgtgc cgtgatggag gaaaccaccc   780
attacaacac cgcgatgatg cgcgcttcac tggaagaagc gagcacggtg cgcgaacgcg    840
tgctggcgct gatccgctgc aagttgcagt cgatcatggg cggcagtggc gaggccatgg    900
cggtgctggt ctacgaatgg cgctcgctgt cggccgaagg ccaggcgcac gtgctggccc    960
tgcgtgacgt gtatgagcag atctggttgc aggtactggg cgaggccaag gccgctggct   1020
acatccgggg cgacgtgttt attacccggc gcttcctcac cggggcctta tcctggacca   1080
ccacctggtt tcgtgcccaa ggcagcctga cccttgagga gttggccgaa gaggccttgt   1140
tgatggtgct gaagtcggac tgaggcgcaa gttattaatt tgctggcgaa agttgtctcc   1200
cccaataaaa acgcctagct tatcggcatt gaactcttca acggtgtgtg cctcgatgtt   1260
ttcgccatgg cggctggctg caggacttac tttatgggca ctgggcaccg ccgcgtggac   1320
gcaggctggt gccgcgcagt tggtgagaat cggcgcggcg cattttccgc cctacaccgt   1380
acgccctgaa caaggcgccg acaccgggtt gctgccgcaa ttggtcgagg cgttgaacgc   1440
tgcgcaaacc gattaccagt ttgtggtggt gcctacctcg atacctcggc gttttcgtga   1500
cttcgagcaa ggccgggtcg acatggcgat cttcgaaaac ccgtcctggg gttggcagaa   1560
tattgcccat accagtgttg atatgggggct gaagatgcgg agattttttgt cgctcagcgt   1620
cagcccggtc gcgaccagag ttattttttcc gacctcaccg gaagcgctgg cggtattcag   1680
cgggtatcac tatgcctttg ctgacttcaa tcccgatccc aagaacatgc cgagcgtttc    1740
aacgcgacgt tgacctactc ccatgacagt aatctgctga tggttgctcg tgggcgtgca    1800
gatattgcgc tggttacccg ctcgtacctg agtgatttca tggtgcgcaa cgcggacatg    1860
gcggggcagt ttttggtgtc ggagcgtatt gaccaggtgt atcaccacta cgcgttgttg    1920
cgnccaaggc acccgatcac tggtccggcg tttgccggaa ctgctcaagt cttgcgcgac    1980
agtggccaga tgctgaagat ttttgagccg tatcgtattg atgtgacgcc ggtgccctaa    2040
ggtcttagta agtaaaatcc ttcgggctca gtgggatcaa ctgtggaagc tggcttgcct   2100
gcgatggcgg cctgacagcc gacacagatt aattgatgct gatgcccgc gatccaatgt    2160
gggagcttgg cttgcctgcg aagacggcct gacagtcaac acagttggac cgtgtacata   2220
tccatccctt gcggtaacgg gctacttagg gttccgcttt tacagcggct cacttttgaa  2280
aagcgcaaaa gtaagcaaaa cgctcttgcc ccaccactcg gcacctcgcc aggctcggtg   2340
tgccccgtaat ccgccagtga tttgggggggc cgcccacgcg catccatgcg cggggcggct   2400
aaacggatcc ctgccggttt acccccccaaa tcccctgtcg aattccggcc agcgtggttt   2460
```

```
aacggggcgc ctaagatcaa aagccagatc aagatcacaa gcagatcaag atcacaagca    2520
gatcaagatc acaagcagat caagatcaca agcagatcaa gatcaagagc gggctcgctt    2580
cgcatcgtag tttccgtgga gcccttaccc acatatgtcg gcgctggatt aaacccgccg    2640
cgcaaacgta tcgctatgac tgcccgacac cttgcggcaa tgcaccagcg catcgcgaat    2700
catgaagttc accaaggtcg gagacacccc aagctccttg gcgatgtctt tttgcggcac    2760
gccatgcaag cggtacatct cgaacgcgta gcgggtgcgc tggggcagtt gcgtcagggc    2820
gtcggcgatg ttttccaggg tgttgaaatt gatgtgcgag gtttccggtg aagcgccgtg    2880
aataaccaca ttcaagcctt cctcttcggt cccggagtat ttgagctcca gggcctgctt    2940
gcggtaatga tcgatcgcca ggttgcgtac gatctgaaac agataactca gttgggccttt   3000 gaacgatgag gtgatggtcg gcgccgactg cagccggaag taggcgtcct gcaccacgtc    3060
ttcggcgcgg gagcggcacc cggtgatacg ggccgcgatc ttcaccagaa tcagtcgatt    3120
gtcgacgaac gcctggagaa ggggtgaatc gcacctgcct gtggatactg gttccgtcat    3180
ggaaatcacc ttgctgcgaa taggttaggg aagggcatcc ctgttaggcc tcctacatat    3240
cgggcaccaa attatgctta atgataatga ttgtcaaatg agaaggcgaa ctaatcttat    3300
gccttggcga aggtgtgaac cacgtctcgc tccccccgg cgactaatta tttgaaggct     3360
ccgtccgttc tcatgggtga caggttcgtt agtacaacgg ccaaggacca gcacccgcag    3420
gaggaccaga tgggttttta tcgtgcattc agcgtgtttc agttcggagt cctcgcggga    3480
tgagtacgtc cctgcggctg cgcctgtttt gcctgcccca ctcaggcgcc agcgcctcgg    3540
tctacgctcg ctggcgccgg gtgctgccgg actggctgca agtgtgcccg ctggaattgc    3600
cgggacgcgg catgcgcatg gacgagccat tgcagcgcga taccagcccg ggccgtc      3657
```

METHODS OF DIAGNOSING AND TREATING CROHN'S DISEASE USING *PSEUDOMONAS* ANTIGENS

This application is based on, and claims the benefit of, U.S. Provisional Application No. 60/240,347, filed Oct. 13, 2000, and entitled Methods of Diagnosing and Treating Crohn's Disease Using *Pseudomonas* Antigens, and which is incorporated herein by reference.

This application was made with government support under grant number DK46763 awarded by the National Institutes of Health. The government has certain rights in the invention.

BACKGROUND OF THE INVENTION

1. Field of the Invention

The invention relates generally to the fields of immunology, microbiology and inflammatory bowel disease and more specifically to the diagnosis and treatment of inflammatory bowel disease using *Pseudomonas* antigens.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increased occurrence of psychological problems, including anxiety and depression, are perhaps not surprising symptoms of what is often a debilitating disease that strikes people in the prime of life.

Unfortunately, the available therapies for inflammatory bowel disease are few, and both diagnosis and treatment have been hampered by a lack of knowledge regarding the etiology of the disease. What is clear, however, is that a combination of genetic factors, exogenous triggers and endogenous microflora can contribute to the immune-mediated damage to the intestinal mucosa seen in inflammatory bowel disease. In Crohn's disease, bacteria have been implicated in initiation and progression of the disease: the intestinal inflammation in Crohn's disease is notable for its frequent responsiveness to antibiotics and susceptibility to bacterial fecal flow. Common intestinal colonists and novel pathogens have been implicated in Crohn's disease by direct detection or by disease associated anti-microbial immune responses. Furthermore, in many genetically susceptible animal models of chronic colitis, lumenal microorganisms are a necessary cofactor for disease; animals housed in a germ-free environment do not develop colitis. However, despite much direct and indirect evidence for a role for enteric microorganisms in Crohn's disease, the pathogenic organisms contributing to the immune dysregulation seen in this disease have not been identified.

Identification of the involved microbial species would provide a basis for the discovery of new antibiotics and other drugs for treating Crohn's disease, such drugs ameliorating disease by eliminating the microbial inducers of disease. Furthermore, identification of the involved microbial species would provide a basis for novel vaccines and for diagnosing Crohn's disease based on the presence of reactivity in patient sera against the identified microbial organisms.

Thus, there is a need for identification of the microbial species that play a role in inflammatory bowel disease such as Crohn's disease. The present invention satisfies this need and provides related advantages as well.

SUMMARY OF THE INVENTION

The present invention provides a method of identifying an agent useful in treating Crohn's disease. This method is practiced by culturing *P. fluorescens* under conditions that support growth; contacting the *P. fluorescens* with an agent; and assaying for reduced growth or viability of the *P. fluorescens* as compared to the growth or viability in the absence of the agent, where the reduced growth or viability of the *P. fluorescens* indicates that the agent is an anti-*P. fluorescens* agent useful in treating Crohn's disease. Such an agent can be, for example, an antibiotic. An effective amount of an anti-*P. fluorescens* agent identified according to a method of the invention can be administered to an individual to prevent or treat Crohn's disease. The anti-*P. fluorescens* agent identified and administered can be, for example, an antibiotic or a combination of two or more antibiotics.

The invention also provides a method of preventing or treating Crohn's disease in an individual by administering to the individual an effective amount of an anti-*Pseudomonas* agent. Such an anti-*Pseudomonas* agent can be, for example, an anti-*P. fluorescens* agent. If desired, an anti-*Pseudomonas* agent can be administered in a manner which is optimized for effectivity against *P. fluorescens*. Anti-*Pseudomonas* agents useful for preventing or treating Crohn's disease include antibiotics such as β-lactamase-resistant penicillin formulations, aminoglycosides and fluoroquinolones. In one embodiment, the anti-*Pseudomonas* agent administered to prevent or treat Crohn's disease is the antibiotic vancomycin. If desired, two or more antibiotics can be administered in combination to prevent or treat Crohn's disease according to a method of the invention.

Further provided by the invention is a method of preventing or treating Crohn's disease in an individual by administering to the individual an effective dose of an anti-*Pseudomonas* vaccine. Such a vaccine can be, for example, an anti-*P. fluorescens* vaccine. Anti-*Pseudomonas* vaccines useful in the invention include killed whole *Pseudomonas* such as killed whole *P. fluorescens*.

In one embodiment, the anti-*Pseudomonas* vaccine is a purified antigen. Thus, the invention additionally provides a method of preventing or treating Crohn's disease in an individual by administering to the individual an effective dose of a purified *Pseudomonas* antigen, or a tolerogenic fragment thereof. In a method of the invention, the purified *Pseudomonas* antigen can be, for example, a purified *P. fluorescens* antigen or a tolerogenic fragment thereof. The methods of the invention can be practiced with a purified *P. fluorescens* antigen such as pbrA, or a tolerogenic fragment thereof. In one embodiment, the methods of the invention are practiced with a purified pbrA antigen having the amino acid sequence SEQ ID NO: 2 or SEQ ID NO: 3, or a tolerogenic fragment of one of these sequences.

A purified *Pseudomonas* antigen, or a tolerogenic fragment thereof, useful in the invention also can be PFTR, or a tolerogenic fragment thereof, provided that the fragment is not I-2 or a fragment thereof. For example, the methods of the invention can be practiced with purified PFTR having the amino acid sequence SEQ ID NO: 5, or a tolerogenic fragment thereof. Additional *Pseudomonas* antigens useful in the invention include, but are not limited to, outer membrane proteins, toxins, lipopolysaccharide (LPS), exotoxin A and TonB and tolerogenic fragments thereof.

Further provided by the invention is a method of preventing or treating Crohn's disease in an individual by administering to the individual an agent that reduces the expression or activity of pbrA, thereby reducing the growth or viability of *P. fluorescens* in the individual. In one embodiment, such an agent reduces the expression of pbrA. Exemplary agents that reduce the expression of pbrA include, without limitation, pbrA antisense nucleic acid molecules and sequence-specific ribonucleases.

The invention additionally provides a method of preventing or treating Crohn's disease in an individual by administering to the individual an agent that reduces the expression or activity of PFTR, thereby reducing the growth or viability of *P. fluorescens* in the individual. Agents which reduce the expression of PFTR include PFTR antisense nucleic acid molecules and sequence-specific ribonucleases. Agents useful in the invention further include inhibitors of PFTR enzymatic function such as inhibitors of ferrodoxin activity, for example, competitive inhibitors of ferrodoxin activity.

The invention also provides a method of diagnosing Crohn's disease in a individual by obtaining a sample from the individual; contacting the sample with pbrA, or an immunoreactive fragment thereof, under conditions suitable to form a complex of pbrA, or the immunoreactive fragment thereof, and antibody to pbrA; and detecting the presence or absence of the complex, where the presence of the complex indicates that the individual has Crohn's disease. In such a diagnostic method of the invention, the presence or absence of the complex can be detected, for example, with a detectable secondary antibody. The methods of the invention can be practiced, for example, with pbrA having the amino acid sequence SEQ ID NO: 2 or SEQ ID NO: 3, or with an immunoreactive fragment of one of these sequences.

The invention also provides a method of diagnosing Crohn's disease in a individual by obtaining a sample from the individual; contacting the sample with PFTR, or an immunoreactive fragment thereof, under conditions suitable to form a complex of PFTR, or the immunoreactive fragment thereof, and antibody to PFTR; and detecting the presence or absence of the complex, provided that the immunoreactive fragment is not I-2 or a fragment thereof, where the presence of the complex indicates that the individual has Crohn's disease. In one embodiment, the presence or absence of the complex is detected with a detectable secondary antibody. In a further embodiment, the diagnostic method of the invention is practiced with PFTR having the amino acid sequence SEQ ID NO: 5, or an immunoreactive fragment thereof.

BRIEF DESCRIPTION OF THE DRAWINGS

FIGS. 4A and B shows the nucleotide (SEQ ID NO: 1) and amino acid sequence (SEQ ID NO: 2) of pbrA-v isolated from a patient with Crohn's disease (UCLA #268).

FIGS. 5A and B shows the nucleotide (SEQ ID NO: 4) and amino acid sequence (SEQ ID NO: 5) of PFTR. Sequences in bold indicate the 2Fe-2S binding domains. The internal portion of PFTR, designated "I-2," is underlined.

FIG. 6 shows *P. fluorescens* genomic sequence (SEQ ID NO: 10) including the PFTR and pbrA loci.

DETAILED DESCRIPTION OF THE INVENTION

The pathogenesis of inflammatory bowel disease, although poorly understood, ultimately involves immune-mediated tissue damage. Similar to autoimmune disorders such as diabetes mellitus and multiple sclerosis, inflammatory bowel disease is associated with various immunologic abnormalities and can represent a process of immune dysfunction. However, unlike the other disorders, inflammatory bowel disease occurs in a mucosal site interfacing with the intestinal lumen, and, therefore, a primary immune target in inflammatory bowel disease can be extrinsic agent such as a chronic microbial colonist. In this case, the mucosal injury characteristic of inflammatory bowel disease is a consequence of inflammatory bystander damage to resident parenchymal cells.

A microbial DNA sequence designated the "I-2" sequence was found preferentially in involved Crohn's disease (CD) mucosa as compared to uninvolved mucosa. Specifically, the I-2 sequence was identified as differentially present in mononuclear cells from the lamina propria in an area with ulcerations as compared to an area macroscopically free of disease (Sutton et al., *Gastroenterology* 119:23–31 (2000). Furthermore, PCR analysis of colonic samples from CD, UC and non-IBD patients revealed that a high I-2 signal was more often found in involved CD tissue than in UC or non-IBD samples although the I-2 sequence was detectable at low levels in biopsy tissue of the ileum in most individuals, including normal individuals as well as those with Crohn's disease.

As disclosed herein, the I-2 sequence is present in some but not all members of the *Pseudomonadaceae* (see Example I). Of a variety of *Pseudomonadaceae* species assayed, *P. fluorescens* contained the I-2 sequence, and related sequences were found in *P. aeruginosa, P. pseudoalcaligenes* and *Shewanella putrefasciens*. The relatively high signal and specific association of *P. fluorescens* I-2 DNA in Crohn's disease colonic lesions, and the occurrence of a disease-specific host response evidenced by anti-I-2 antibodies, indicate that *P. fluorescens* is particularly successful as a colonist in Crohn's disease. As further disclosed herein in Example II, *P. fluorescens* but not other individual bacterial species can substitute for a complete mixture of intestinal microbiota (cecal lumenal contents) in CD4+

CD45RBhi mice, which require enteric bacteria as a pathogenic cofactor in order to develop colitis. These results indicate that *P. fluorescens*, unlike typical intestinal microflora, can be pathogenic in colitis-susceptible individuals. These results further indicate that vaccines and agents that reduce or eradicate *P. fluorescens* can be useful for the treatment and prevention of colitis.

Figure 2:
FIG. 2 shows an alignment of pbrA-v, pbrA, pvdS and pfrI proteins, which are members of an iron-responsive gene family. The predicted pbrA sequence isolated from UCLA #268 ("pbrA-v;" SEQ ID NO: 2) is shown compared to pbrA of *P. fluorescens* ("pbrA;" SEQ ID NO: 3); pvdS of *P. aeruginosa* ("pvdS;" SEQ ID NO: 7) and pfrI of *P. putida* ("pfrI;" SEQ ID NO: 8). A consensus sequence is shown as SEQ ID NO: 9. Alignment was performed with ClustalW, and the results displayed using genDoc. The variable region at the extreme C-terminus is indicated.
Figure 3:
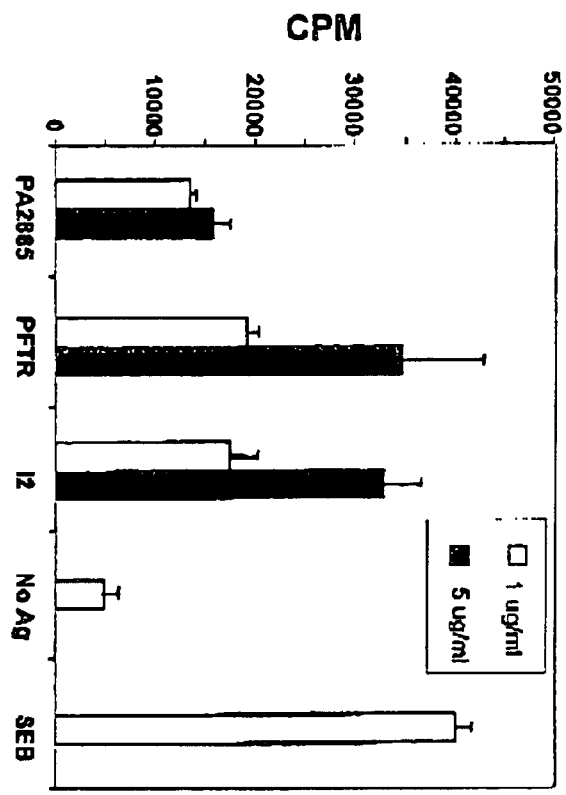
FIG. 3 shows stimulation of $CD4^+$ T cell proliferation with microbial antigens. $CD4^+$ T cells from C57BL/6J mice were cultured with syngeneic APCs previously pulsed with recombinant I-2, PFTR, or PA2885 protein at 1 and 5 µg/mL. SEB (1 µg/mL) was used as the positive control. Proliferation was assayed after 72 hours in triplicate cultures.

Additional results disclosed herein indicate that the I-2 sequence is the internal portion of the *P. fluorescens* sequence PFTR. As shown in FIG. 2, *P. fluorescens* and *P. aeruginosa* were homologous for several open reading frames, including, in *P. fluorescens*, pbrA, which encodes an iron-regulated transcription factor. As shown in FIG. 3, comparison of pbrA from *P. fluorescens* to homologous gene products from other microorganisms indicated strong conservation across the protein sequence except for a divergent carboxy-terminus (see Example III). These results indicate that vaccines or therapeutics that reduce the expression or activity of highly conserved *P. fluorescens* gene products, such as pbrA or PFTR, can be useful in preventing and treating Crohn's disease.

As further disclosed herein, His-tagged I-2, PFTR and the *P. aeruginosa* homologue PA2885 were assayed for the ability to stimulate CD4+ T cell proliferation. Following preincubation of the proteins with antigen-presenting cells, both I-2 and PFTR strongly stimulated CD4+ T cell proliferation, while the *P. aeruginosa* homologue of PFTR (PA2885) was much less active. These results support a role for *P. fluorescens* in immune-mediated pathology. In sum, the results described herein make possible new methods of screening for effective Crohn's disease therapeutics, as well as new methods of diagnosing and ameliorating Crohn's disease.

Thus, the present invention provides a method of identifying an agent useful in treating Crohn's disease. This method is practiced by culturing *P. fluorescens* under conditions that support growth; contacting the *P. fluorescens* with an agent; and assaying for reduced growth or viability of the *P. fluorescens* as compared to the growth or viability in the absence of the agent, where the reduced growth or viability of the *P. fluorescens* indicates that the agent is an anti-*P. fluorescens* agent useful in treating Crohn's disease. Furthermore, an effective amount of an anti-*P. fluorescens* agent identified according to a method of the invention can be administered to an individual to prevent or treat Crohn's disease. The anti-*P. fluorescens* agent identified and administered can be, for example, an antibiotic or a combination of two or more antibiotics.

As used herein, the term "agent" means a biological or chemical compound such as a simple or complex organic molecule, a peptide, a protein, an antibody, a lipid, a nucleic acid molecule or an oligonucleotide.

As used herein, the term "agent useful in treating Crohn's disease" means an agent that reduces the severity, frequency, or time of onset of one or more symptoms of Crohn's disease.

An agent identified by the methods of the invention reduces the growth or viability of *P. fluorescens*, which, as disclosed herein, can be a factor contributing to development or progression of Crohn's disease. Such an agent is useful in treating Crohn's disease and can be a bacteriostatic or bacteriocidal agent such as a bacterial antibiotic, which is a molecule that can reduce the growth or viability of a bacterial species and which can be produced, for example, by a microorganism or a plant.

One skilled in the art understands that an agent useful in treating Crohn's disease can function by a variety of mechanisms, for example, by inhibiting *P. fluorescens* protein synthesis, inhibiting *P. fluorescens* DNA synthesis, inhibiting *P. fluorescens* cell wall synthesis or inhibiting synthesis of an essential nutrient of *P. fluorescens*. It is understood that such an agent can selectively reduce the growth or viability of *P. fluorescens* or can have activity in reducing the growth or viability of other species of the *Pseudomonadaceae* or other microbes. One skilled in the art understands that, preferably, an agent useful in treating Crohn's disease reduces the growth or viability of *P. fluorescens* without significantly altering the growth or viability of mammalian cells, especially human cells.

Identification of *P. fluorescens* as the microbe carrying a sequence found preferentially in involved Crohn's disease (CD) mucosa as compared to uninvolved mucosa implicates this organism in the pathogenesis of Crohn's disease. Furthermore, *P. fluorescens*, alone, can substitute for a complete mixture of intestinal microbiota in conferring disease in colitic CD4+CD45RBhi mice, further evidencing the importance of this microorganism in initiation or progression of Crohn's disease. These results provide the basis for new methods of ameliorating Crohn's disease.

In particular, the present invention provides a method of preventing or treating Crohn's disease in an individual by administering to the individual an effective amount of an anti-*Pseudomonas* agent. Such an anti-*Pseudomonas* agent can be, for example, an anti-*P. fluorescens* agent. If desired, an anti-*Pseudomonas* agent can be administered in a manner which is optimized for effectivity against *P. fluorescens*. Anti-*Pseudomonas* agents useful for preventing or treating Crohn's disease include antibiotics such as β-lactamase-resistant penicillin formulations, aminoglycosides and fluoroquinolones. In one embodiment, the anti-*Pseudomonas* agent administered to prevent or treat Crohn's disease is the antibiotic vancomycin. If desired, two or more antibiotics can be administered in combination to prevent or treat Crohn's disease according to a method of the invention.

As used herein, the term "anti-*Pseudomonas* agent" means an agent that produces a detectable reduction in the growth or viability of one or more species of Pseudmonas.

The term "anti-*P. fluorescens* agent" means an agent that produces a detectable reduction in the growth or viability of *P. fluorescens*. Such agents typically produce an in vitro as well as in vivo reduction in the growth of viability of *P. fluorescens*. An anti-*P. fluorescens* agent useful in the invention can produce, for example, at least a 10%, 25%, 50%, 75% or 100% reduction in the growth or viability of *P. fluorescens* in an individual to whom the agent is administered.

As used herein, the term "effective amount" means the amount of an anti-*P. fluorescens* agent useful for reducing the growth or viability of *P. fluorescens* in the individual.

As used herein, the term "individual" means any animal capable of having inflammatory bowel disease, including a human, non-human primate, rabbit, rat or mouse. An individual can have one or more symptoms of ulcerative colitis or Crohn's disease, or can be asymptomatic or disease free. The term individual includes normal individuals that do not have inflammatory bowel disease and individuals that do not have ulcerative colitis or Crohn's disease but who are susceptible to one of these diseases.

At least three categories of antibiotics are active against *Pseudomonas*. These categories include penicillin/β-lactamase-resistant formulations such as piperacillin-tazobactam; aminoglycosides such as amikacin; and fluoroquinolones such as ciprofloxacin. Antibiotics useful as anti-

*Pseudomonas* agents in the methods of the invention include, for example, vancomycin, which can be administered, if desired, as a two week course by intravenous administration. These and other antibiotics that reduce the growth or viability of one or more species of *Pseudomonas* are known in the art, as described, for example, in Lister et al., *Pharmacotherapy* 20:213S-8S (2000) and Yamaguchi et al., *Japanese J. Antibiot.* 53:387–408 (1998). In one embodiment, a method of the invention is practiced by administering two or more antibiotics from two or more of the above three categories.

It is understood that an anti-*Pseudomonas* agent can be a broad range antibiotic that effects the growth or viability of many or all species of *Pseudomonas*, or can be selective or specific. A selective anti-*P. fluorescens* antibiotic reduces the growth or viability of *P. fluorescens* with little or no effect on most other members of the *Pseudomonadaceae*. Such a selective anti-*P. fluorescens* antibiotic can, for example, reduce the growth or viability of *P. fluorescens* with little or no effect on *P. aeruginosa*. In one embodiment, the anti-*Pseudomonas* agent is administered to an individual lacking symptoms of bacterial infection that would generally warrant administration of an antibiotic. In a further embodiment, an antibiotic such as ciprofloxacin or vancomycin is administered to an individual having Crohn's disease but lacking symptoms of bacterial infection that would generally warrant administration of an antibiotic.

Further provided by the invention is a method of preventing or treating Crohn's disease in an individual by administering to the individual an effective dose of an anti-*Pseudomonas* vaccine. Such a vaccine can be, for example, an anti-*P. fluorescens* vaccine. Anti-*Pseudomonas* vaccines useful in the invention include killed whole *Pseudomonas* such as killed whole *P. fluorescens*.

*Pseudomonas* vaccines can be, for example, whole killed cell preparations as described in Cripps et al., *Behring Inst. Mitt.* 262–8 (1997). Outer membrane protein vaccines can be prepared against *P. fluorescens* or other *Pseudomonadaceae*, for example, as described in Lee et al., *Vaccine* 18:1952–61 (2000), and Lee et al., *FEMS Immunol Med. Microbiol.* 27:79–85 (2000); Knapp et al., *Vaccine* 17:1663–6 (1999); and Mansouri et al., *Infect. Immun.* 67:1461–70 (1999).

Synthetic peptides and proteins, for example, pbrA and PFTR and fragments thereof, as described further below, also can be used to prepare a *Pseudomonas* vaccine useful in the invention. See, for example, Cachia et al.,*J. Pept. Res.* 52:289–99 (1998) and Gilleland et al., *Curr. Microbiol.* 31:279–86 (1995). It is understood that an immune response induced by a *Pseudomonas* vaccine can be directed against a variety of species of the *Pseudomonadaceae*, or can be relatively specific, for example two-fold or more stronger against *P. fluorescens* than other bacterial species such as *P. aeruginosa*. Lipopolysaccharides (LPS) and toxins also can be useful antigenic preparations to be used in the methods of the invention. See, for example, Stanislavsky et al., *FEMS Immunol Med. Microbiol.* 18:139–45 (1997); Lang et al., *J. Pediatr.* 127:711–7 (1995); and Cryz et al., *Vaccine* 13:449–53 (1995). The use of these and other *Pseudomonas* antigens as vaccines is known in the art, as described, for example, in Stanislavsky, *FEMS Microbiol. Rev.* 21:243–77 (1997). The sequences of *Pseudomonas* antigens to be used in a DNA vaccine, to prepare recombinant purified antigen or to prepare a genetically engineered cellular vaccine are known in the art and are disclosed herein as, for example, SEQ ID NOS: 1 to 5 (see, also, Stover et al., *Nature* 406:959–964).

A cell useful in preparing an anti-*Pseudomonas* vaccine useful in the invention can be any prokaryotic or eukaryotic cell capable of having expressed on its cell surface a *Pseudomonas* antigen. The term cell includes live, attenuated and killed cells and encompasses primary cells, normal cells, and immortalized or transformed cells. In the methods of the invention, a cell can be autologous, allogeneic or xenogeneic to the patient to whom the vaccine is administered. Cellular vaccines useful in the invention can be prepared, for example, from bacterial cells such as *Escherichia coli*, Salmonella, *Listeria monocytogenes* and *Mycobacterium bovis*. Such cells can be genetically modified by routine methods to express a *Pseudomonas* antigen or fragment thereof in order to produce a vaccine useful in the invention.

Transformed and non-transformed cells including fibroblasts, myoblasts, leukocytes, hepatocytes, endothelial cells and dendritic cells, and especially human cells, can be used to prepare a vaccine expressing a *Pseudomonas* antigen or immunogenic fragment thereof. Fibroblasts useful in the invention include autologous fibroblasts obtained from the individual to be vaccinated. Such primary human fibroblasts are readily obtained, for example, by punch biopsy of the skin, or from tissues such as lung, liver or bone marrow. Fibroblasts can be readily cultured and propagated in vitro (Treco et al., "Fibroblast Cell Biology and Gene Therapy," in Chang (Ed.), *Somatic Gene Therapy* CRC Press, Boca Raton (1995)).

Bacterial cells also are useful in preparing an anti-*Pseudomonas* vaccine. Live bacterial vaccines using, for example, attenuated strains of bacteria are useful in the invention since such live vaccines generally can confer a stronger, longer-lasting immune response than killed vaccines. Live bacterial vaccines can establish limited infections in the host that mimic the early stages of natural infection and lead to a natural immune response, and can confer extended immunity since the bacteria remain viable in the host for a long time. In addition, bacterial outer membrane proteins, lipopolysaccharides (LPS) and secreted bacterial toxins are strongly immunogenic and can act as natural adjuvants to enhance an immune response against a recombinant antigen. Furthermore, such live bacterial vaccines are easily administered, for example, orally.

A variety of avirulent bacterial strains have been developed for use as live vaccines. Bacteria useful in an anti-*Pseudomonas* vaccine include, without limitation, Salmonellae, *Vibrio cholerae, Mycobacterium bovis* (e.g. Bacillus Calmette-Guerin (BCG)), *Streptococcus gordonii, Escherichia coli, shigella, lactobacillus, Listeria monocytogenes* and *Bacillus subtilis* (see, for example, Curtiss, "Attenuated Salmonella Strains as Live Vectors for the Expression of Foreign Antigens," in Woodrow and Levine (Ed.), *New Generation Vaccines* Marcel Dekker, Inc. (1990); Cardenas and Clements, *Clin. Microbiol. Rev.* 5:328–342 (1992); Cirillo et al., *Clin. Infect. Dis.* 20:1001–1009 (1995); Fortaine et al., *Res. Microbiol.* 141:907–912 (1990); Irvine and Restifo, *Seminars in Cancer Biology* 6:337–347 (1995); and Stover et al, *Nature* 351:456–460 (1991)). Bacteria useful in an anti-*Pseudomonas* vaccine also include *Shigella flexneri, Yersinia enterocolitica, bordetella pertussis* and *Staphylococcus xylosus* (Ryd et al., *Microbiol. Pathogen.* 12:399–407 (1992); van Damme et al., *Gastroenterol.* 103:520–531 (1992); and Renauld-Mongenie et al., *Proc. Natl. Acad. Sci., USA* 93:7944–7949 (1996)). Yeast cells such as *Saccharomyces cerevisiae* also can be useful in anti-*Pseudomonas* vaccine, particularly in expressing *Pseudomonas* antigens that require post-translational modifications for activity.

Salmonella cells can be useful in preparing an anti-*Pseudomonas* vaccine to be used in a method of the invention. Salmonella strains with mutations in genes such as aroA, aroC, aroD, cya, crp, galE, and phoP/phoQ are unable to sustain proliferation within mammalian cells. However, such live attenuated strains grow intracellularly long enough to stimulate an immune response. Attenuated Salmonella strains include nutritional auxotrophs such as those that are defective in biosynthesis of aromatic metabolites and that render the organism auxotrophic for PABA and 2,3-dihydroxybenzoate. These attenuated strains have mutations in the aro genes, for example, deletions in one or more of the aroA, aroC or aroD genes. Deletions in adenylate cyclase (cya) and cyclic 3',5'-AMP receptor protein (crp) genes also are useful in generating attenuated Salmonella strains. Live attenuated Salmonella vaccines can be prepared using, for example, *S. typhimurium* strains such as ΔaroA ΔaroD BRD509, ISP1820ΔaroC ΔaroD, Ty2ΔaroC ΔaroD and Ty2Δcya Δcrp (see, for example, Tacket et al., *Infect. Immun.* 60:536–541 (1992); Turner et al., *Infect. Immun.* 61:5374–5380 (1993); Dunstan et al., *Infect. Immun.* 64:2730–2736 (1996); Londoño et al., *Vaccine* 14:545–552 (1996)). Expression vectors for use in Salmonella include pKK233-2 and are well known in the art (Amann and Brosius, *Gene* 40:183–190 (1985); see, also, Anderson et al., "Development of Attenuated Salmonella Strains that Express Heterologous Antigens" in Robinson et al., *Methods in Molecular Medicine: Vaccine Protocols* Humana Press, Inc. Totowa, N.J.).

*Listeria monocytogenes* also are bacteria useful in preparing an anti-*Pseudomonas* vaccine. *L. monocytogenes* can be readily engineered to express a *Pseudomonas* antigen as described, for example, in Paterson and Ikonomidis, *Curr. Opin. Immunol.* 8:664–669 (1996)).

*Lactococcus lactis* also can be useful in preparing an anti-*Pseudomonas* vaccine. *L. lactis* is a non-pathogenic and non-colonizing bacterium useful as a vaccine delivery vehicle, particularly for immunization by mucosal routes. *L. lactis* strains have been produced which express recombinant antigen, and also optionally secrete an immunostimulatory cytokine, such as interleukin-2 or interleukin-6. Intranasal immunization with recombinant *L. lactis* results in high intestinal titers of antibodies directed against such recombinantly expressed antigens (Steidler et al., *Infect. Immun.* 66:3183–3189 (1998)). One skilled in the art understands that these and other prokaryotic and eukaryotic host cells can be used to prepare an anti-*Pseudomonas* vaccine useful in the methods of the invention.

Expression vectors useful in the anti-*Pseudomonas* vaccines of the invention include prokaryotic and eukaryotic expression vectors. Such expression vectors, including plasmids, cosmids, and viral vectors such as bacteriophage, baculovirus, retrovirus and DNA virus vectors, are well known in the art (see, for example, *Meth. Enzymol.*, Vol. 185, D. V. Goeddel, ed. (Academic Press, Inc., 1990) and Kaplitt and Loewy (Ed.), *Viral Vectors: Gene Therapy and Neuroscience Applications* (Academic Press, Inc., 1995)). Expression vectors contain the elements necessary to achieve constitutive or inducible transcription of a nucleic acid molecule encoding the desired *Pseudomonas* antigen. Eukaryotic expression vectors that result in high levels of sustained expression, such as vectors including cytomegalovirus (CMV), rous sarcoma virus (RSV), or simian virus 40 (SV40) promoter/enhancer elements, are particularly useful in preparing an anti-*Pseudomonas* vaccine.

An expression vector encoding a *Pseudomonas* antigen can be introduced into a cell to produce an anti-*Pseudomonas* vaccine by any of a variety of methods known in the art and described, for example, in Sambrook et al., *Molecular Cloning: A Laboratory Manual*, 2nd Ed, Vols 1 to 3, Cold Spring Harbor Laboratory Press, New York (1989), and in Ausubel et al., *Current Protocols in Molecular Biology*, John Wiley and Sons, Baltimore, Md. (1994). Such methods include, without limitation, lipofection and electroporation.

The number of vaccine cells to be administered to an individual according to a method of the invention is the number of cells that can modulate an immune response against *Pseudomonas*. Such an immune response can reduce the growth or viability of enteric *Pseudomonas* in the individual and can alleviate one or more symptoms of Crohn's disease. An effective number of vaccine cells to be administered can be determined by monitoring the *Pseudomonas* bacterial load in the individual before and after treatment, or by monitoring one or more well known parameters for monitoring the course of Crohn's disease. In general, a vaccine containing approximately $1 \times 10^4$ to $1 \times 10^8$ cells, for example, $1 \times 10^7$ to $1 \times 10^8$ cells, is an effective dose. One skilled in the art understands that the number of vaccine cells to be administered depends, for example, on the number of times the vaccine is to be administered and the level of response desired.

An anti-*Pseudomonas* vaccine can be administered, if desired, with a pharmacologically acceptable solution such as physiological saline or with an appropriate adjuvant. Numerous pharmacologically acceptable solutions and adjuvants useful for immunization are known within the art. It is recognized that the anti-*Pseudomonas* vaccine should be stable in such solutions or adjuvants.

Vaccine administration can be accomplished by any of various methods including, without limitation, subcutaneous, intradermal, intramuscular, oral, intranasal and rectal administration. Immune responses are generally anatomically restricted, with the gastrointestinal and nasal sites containing a lymphocyte population that shares these two sites for trafficking and biologic activity. In one embodiment, the anti-*Pseudomonas* vaccine is administered to induce an immune response directed to the gastrointestinal and nasal sites. In another embodiment, the anti-*Pseudomonas* vaccine is administered orally, intranasally, or rectally. In a further embodiment, the anti-*Pseudomonas* vaccine is administered orally. In yet a further embodiment, the anti-*Pseudomonas* vaccine is administered intranasally. It is recognized that booster vaccines administered, for example, every several months, also can be useful in preventing or treating Crohn's disease according to a method of the invention.

In one embodiment, the invention additionally provides a method of preventing or treating Crohn's disease in an individual by administering to the individual an effective dose of a purified *Pseudomonas* antigen, or a tolerogenic fragment thereof. In such a method, the purified *Pseudomonas* antigen can be, for example, a purified *P. fluorescens* antigen or a tolerogenic fragment thereof. A purified *P. fluorescens* antigen useful in the invention can be, for example, pbrA, or a tolerogenic fragment thereof. Such a purified pbrA antigen can have, for example, the amino acid sequence SEQ ID NO: 2 or the amino acid sequence SEQ ID NO: 3, or a tolerogenic fragment of one of these sequences.

A purified *Pseudomonas* antigen, or a tolerogenic fragment thereof, useful in an anti-*Pseudomonas* vaccine also can be PFTR, or a tolerogenic fragment thereof, provided that the fragment is not I-2 or a fragment thereof. In such a method, the purified PFTR can have, for example, the amino acid sequence SEQ ID NO: 5, or a tolerogenic fragment thereof, provided that the fragment is not I-2 or a fragment thereof. Additional *Pseudomonas* antigens useful in the invention include, but are not limited to, outer membrane proteins, toxins, lipopolysaccharide (LPS), exotoxin A and TonB and immunogenic fragments thereof. It is understood that any of a variety of purified *Pseudomonas* antigens, other than the I-2 antigen and fragments thereof, are useful in the methods of the invention. The I-2 sequence is shown as the underlined portion of the PFTR sequence shown in FIG. 5.

The term "purified," as used herein in reference to a *Pseudomonas* antigen, means a polypeptide that is in a form that is relatively free from contaminating lipids, polypeptides, nucleic acids or other cellular material normally associated with the antigen in a cell.

As used herein, the term "pbrA" means a polypeptide having substantially the same amino acid sequence as the *P. fluorescens* pbrA polypeptide SEQ ID NO: 2 or the *P. fluorescens* pbrA polypeptide SEQ ID NO: 3 shown in FIG. 2. The pbrA-v antigen (SEQ ID NO: 2) isolated from patient UCLA #268, which is a polypeptide of 183 amino acids, is an exemplary "pbrA" antigen disclosed herein. In nature, pbrA is required for upregulation of gene products, including siderophores and exotoxins, and facilitates the iron deprivation response by acting as a sigma factor for transcription units bearing a 12 nucleotide PAD box, usually in concert with iron starvation and Fur regulatory factors. Furthermore, pbrA is an iron regulatory sigma factor and an important virulence factor, for example, in endocarditis (Xiong et al., *J. Infect. Dis.* 181:1020–1026 (2000)). The promoters of pbrA and related genes can include a ferric uptake regulator (Fur) box, and can be upregulated by iron starvation through release of the iron-dependent Fur transcription inhibitor.

A pbrA polypeptide can have substantially the same amino acid sequence as SEQ ID NO: 2 or SEQ ID NO: 3. Such a pbrA polypeptide can be a naturally occurring pbrA polypeptide such as SEQ ID NO: 2 or SEQ ID NO: 3, or a related polypeptide having substantial amino acid sequence similarity to one of these sequences. Such related polypeptides can exhibit greater sequence similarity to SEQ ID NO: 2 or SEQ ID NO: 3 than to homologous sigma factors from microbial organisms outside the *Pseudomonas* family and include isotype variants and homologs such as *Pseudomonas* homologs of the amino acid sequences shown as SEQ ID NOS: 2 and 3 in FIG. 2. In one embodiment, a pbrA polypeptide exhibits greater similarly to SEQ ID NO: 2 or SEQ ID NO: 3 than to the *P. aeruginosa* protein pvdS (SEQ ID NO: 7). As used herein, the term pbrA generally describes polypeptides having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with SEQ ID NO: 2 or SEQ ID NO: 3, said amino acid identity determined with CLUSTALW using the BLOSUM 62 matrix with default parameters.

As used herein, the term "PFTR" means a polypeptide having substantially the same amino acid sequence as the *P. fluorescens* polypeptide (SEQ ID NO: 5) shown in FIG. 5. The *P. fluorescens* PFTR polypeptide (SEQ ID NO: 5) is a polypeptide of 198 amino acids sharing some similarity to bacterial ferrodoxins, which are proteins or protein domains that bind to iron-sulfur clusters and mediate electron transfer in a variety of metabolic reactions. Examples of ferrodoxins include *Escherichia coli* formate hydrogenylase, which has two subunits that each contain two 4Fe-4S ferrodoxin-like domains, and the *E. coli* anaerobic glycerol-3-phosphate dehydrogenase, which contains two ferrodoxin-like domains.

A PFTR polypeptide having substantially the same amino acid sequence as SEQ ID NO: 5 can be the naturally occurring *P. fluorescens* PFTR polypeptide (SEQ ID NO: 5) or a related polypeptide having substantial amino acid sequence similarity to this sequence. Such related polypeptides exhibit greater sequence similarity to the PFTR polypeptide SEQ ID NO: 5 than to ferrodoxins outside the *Pseudomonas* family and include isotype variants and homologs such as *Pseudomonas* homologs of the amino acid sequence shown in FIG. 5. As used herein, the term PFTR generally describes polypeptides having an amino acid sequence with greater than about 50% identity, preferably greater than about 60% identity, more preferably greater than about 70% identity, and can be a polypeptide having greater than about 80%, 90%, 95%, 97%, or 99% amino acid sequence identity with SEQ ID NO: 5, said amino acid identity determined with CLUSTALW using the BLOSUM 62 matrix with default parameters.

An effective dose of a purified *Pseudomonas* antigen or a tolerogenic fragment thereof for preventing or treating Crohn's disease can be administered by various methods well known in the art. Oral tolerance is well-recognized in the art as a method of treating autoimmune disease (see, for example, Weiner, *Hospital Practice*, pp. 53–58 (Sep. 15, 1995)). For example, orally administered autoantigens suppress several experimental autoimmune models in a disease- and antigen-specific fashion; the diseases include experimental autoimmune encephalomyelitis, uveitis, and myasthenia, collagen- and adjuvant-induced arthritis, and diabetes in the NOD mouse (see, for example, Weiner et al., *Ann. Rev. Immunol.* 12:809–837 (1994)). Furthermore, clinical trials of oral tolerance have produced positive results in treating multiple sclerosis, rheumatoid arthritis and uveitis. In addition, parenteral administration of a *Pseudomonas* antigen, or a tolerogenic fragment thereof, can be used in the methods of the invention, as can subcutaneous injection (Johnson, *Ann. Neurology* 36(suppl.):S115–S117 (1994)). Multiple smaller oral doses, or a single larger dose, can be administered in the methods of the invention. Such doses can be extrapolated, for example, from the induction of tolerance in animal models (see, for example, Trentham et al., *Science* 261:1727–1730 (1993)).

Further provided by the invention is a method of preventing or treating Crohn's disease in an individual by administering to the individual an agent that reduces the expression or activity of pbrA, thereby reducing the growth or viability of *P. fluorescens* in the individual. In one embodiment, such an agent reduces the expression of pbrA. Exemplary agents that reduce the expression of pbrA include, without limitation, pbrA antisense nucleic acid molecules and sequence-specific ribonucleases.

The invention additionally provides a method of preventing or treating Crohn's disease in an individual by administering to the individual an agent that reduces the expression or activity of PFTR, thereby reducing the growth or viability of *P. fluorescens* in the individual. Agents useful in the invention include agents which reduce the expression of PFTR such as PFTR antisense nucleic acid molecules and sequence-specific ribonucleases. Agents useful in the invention further include inhibitors of PFTR enzymatic function such as inhibitors of ferrodoxin activity. Such an agent can be, for example, a competitive inhibitor of ferrodoxin activity, or a modifier of protein phosphorylation (see, for example, Siegel et al., *J. Biol. Chem.* 261:16998–17003 (1986).

An agent that reduces the expression or activity of pbrA also can be an antisense nucleic acid molecule that down-regulates pbrA expression. Such an antisense nucleic acid molecule can reduce mRNA translation or increase mRNA degradation of pbrA mRNA or the mRNA of a regulatory molecule that positively modulates the expression or activity of pbrA. In one embodiment, a method of the invention is practiced with a pharmaceutical composition containing a pbrA antisense nucleic acid molecule.

Similarly, an agent that reduces the expression or activity of PFTR also can be an antisense nucleic acid molecule that down-regulates PFTR expression. Such an antisense nucleic acid molecule can reduce mRNA translation or increase mRNA degradation of PFTR mRNA or the mRNA of a regulatory molecule that positively modulates the expression or activity of PFTR. In one embodiment, a method of the invention is practiced with a pharmaceutical composition containing a PFTR antisense nucleic acid molecule.

The term "antisense nucleic acid molecule" as used herein, means a nucleic acid molecule that is complementary in sequence to all or part of a molecule of messenger RNA or another specific RNA transcript. Thus, a pbrA antisense nucleic acid molecule is complementary to some or all of a pbrA mRNA such as SEQ ID NO: 1. Similarly, a PFTR antisense nucleic acid molecule is complementary to some or all of a PFTR mRNA such as SEQ ID NO: 4. An antisense nucleic acid molecule can be, for example, DNA or RNA, and can include naturally occurring nucleotides as well as synthetic nucleotides or other non-naturally occurring modifications such as modifications to the phosphate backbone that improve stability. Antisense oligonucleotides, including phosphorothioate and other modified oligonucleotides, are encompassed by the term antisense nucleic acid molecule as used herein.

An antisense nucleic acid molecule useful in the invention can, for example, reduce mRNA translation or increase mRNA degradation, thereby reducing expression of the target mRNA such as a *P. fluorescens* pbrA. An antisense nucleic acid molecule can be perfectly complementary to the target nucleic acid sequence, for example, in a pbrA mRNA, or can contain one or mismatches relative to the endogenous nucleic acid sequence. The homology requirement for reduction of expression using antisense methodology can be determined empirically. Generally, at least about 80–90% nucleic acid sequence identity is present in an antisense nucleic acid molecule useful in the invention, with higher nucleic acid sequence identity often used in antisense oligonucleotides, which can have, for example, 100% identity. The target sequence can be chosen, if desired, to have a small single-stranded region at which nucleation takes place, plus a double-stranded, helically ordered stem that is invaded by the antisense molecule to displace one of the strands (Mir and Southern, *Nature Biotech.* 17:788–792 (1999). Methods for selecting and preparing antisense nucleic acid molecules are well known in the art and include in silico approaches (Patzel et al. *Nucl. Acids Res.* 27:4328–4334 (1999); Cheng et al., *Proc. Natl. Acad. Sci., USA* 93:8502–8507 (1996); Lebedeva and Stein, *Ann. Rev. Pharmacol. Toxicol.* 41:403–419 (2001); Juliano and Yoo, *Curr. Opin. Mol. Ther.* 2:297–303 (2000); and Cho-Chung, *Pharmacol. Ther.* 82:437–449 (1999)).

A pbrA antisense nucleic acid molecule can include, for example, at least 10 contiguous nucleotides complementary to the pbrA sequence shown as SEQ ID NO: 1, or another pbrA encoding sequence or control sequence or a 5' or 3' untranslated sequence. A pbrA antisense nucleic acid molecule also can include, for example, at least 10, 15, 20, 25, 30, 35, 40, 45, 50, 100, 200, 300, 500 or more contiguous nucleotides complementary to SEQ ID NO: 1 or another pbrA encoding sequence or control sequence or a 5' or 3' untranslated sequence. If desired, an antisense nucleic acid molecule can be complementary to the full-length of the target message. Similarly, a PFTR antisense nucleic acid molecule useful in the invention can include, for example, at least 10, 15, 20, 25, 30, 35, 40, 45, 50, 100, 200, 300, 500 or more contiguous nucleotides complementary to the PFTR sequence shown as SEQ ID NO: 4 or another PFTR encoding sequence or control sequence or a 5' or 3' untranslated sequence. Antisense oligonucleotides useful in the invention, including phosphorothioate and other oligonucleotides with otherwise modified backbones, can have, for example, from 12 to 100 nucleotides, for example, from 12 to 50 or from 12 to 30 nucleotides, or from 15 to 100, 15 to 50 or 15 to 30 nucleotides, or from 20 to 100, 20 to 50 or 20 to 30 nucleotides complementary to pbrA or PFTR, for example, complementary to the pbrA sequence shown as SEQ ID NO: 1 or the PFTR sequence shown as SEQ ID NO: 4. Antisense oligonucleotides useful in the invention can have, for example, 18, 19, 20, 21, 22, 23, 24, 25, 26, 27, 28, 29 or 30 nucleotides complementary, for example, to the pbrA sequence shown as SEQ ID NO: 1 or the PFTR sequence shown as SEQ ID NO: 4.

In one embodiment, the antisense nucleic acid molecule is a nuclease-resistant nucleic acid molecule with a modified backbone such as a phosphorothiorate oligodeoxynucleotide, in which a sulfur atom is substituted for a nonbridging oxygen at each phosphorus. Antisense nucleic acid molecules useful in the invention further include, without limitation, mixed backbone oligonucleotides such as phosphorothioate oligodeoxynucleotides containing segments of 2'-O-methyloligoribonucleotides (2'-O-meRNA) or methylphosphonate oligodeoxynucleotides (me-PDNA), which are more resistant to nucleases and form more stable duplexes with RNA than the corresponding phosphorothioate oligodeoxynucleotide (Cho-Chung, supra, 1999); and chimeric antisense oligonucleotides (denoted "gap-mers") containing a "central core" of several consecutive oligodeoxy-containing bases and 2°-O-alkylloligoribonucleotides (methyl or methoxyethoxy) modifications incorporated into the remaining bases and with the backbone composed entirely of phosphorothioate linkages. For example, a central core of 6 to 8 oligodeoxyribonucleotides can be flanked by 6 to 8 2'-O-alkylloligoribonucleotides at the 5' and 3' ends.

While not wishing to be bound by the following, antisense activity can result from cleavage of the mRNA strand by RNase H at the site of hybridization. Thus, in one embodiment, the antisense nucleic acid molecule includes a backbone portion that is RNase H competent. Such competent backbones have phosphodiester or phosphorothioate linkages and deoxyribose sugar moieties. Uncharged backbones, for example, methylphosphonate or peptide nucleic acid linkages, or 2'-O-methylribose or another substitution at the 2' position, are not competent for cleavage by RNase H.

An agent that reduces the expression or activity of pbrA or PFTR also can be a sequence-specific ribonuclease that down-regulates pbrA or PFTR expression, respectively. Such a sequence-specific ribonuclease can catalyze, for example, the specific cleavage of pbrA mRNA or PFTR mRNA or the mRNA of a regulatory molecule that positively modulates the expression or activity of pbrA or PFTR. In one embodiment, a method of the invention is practiced with a sequence-specific ribonuclease, such as a ribozyme, that down-regulates pbrA expression by cleaving pbrA RNA. In another embodiment, a method of the invention is practiced with a sequence-specific ribonuclease, such as a ribozyme, that down-regulates PFTR expression by cleaving PFTR RNA.

The term "sequence-specific ribonuclease," as used herein, means a molecule that catalyzes the cleavage of RNA at a defined ribonucleotide sequence. A sequence-specific ribonuclease can be, for example, a ribozyme or a DNA enzyme. As used herein, the term "ribozyme" refers to a RNA molecule that catalyzes the cleavage of RNA at a defined ribonucleotide sequence.

The specificity of ribozymes such as hammerheads and hairpins for a target cleavage site such as a site present in pbrA or PFTR is determined by base-pairing between the ribozyme and its RNA target. A hammerhead ribozyme, for example, cleaves after "UX" dinucleotides, where X is any ribonucleotide except guanosine, with a higher rate of cleavage when X is cytosine. "NUX" triplets generally are present in the target sequence, where N is any ribonucleotide, and GUC, CUC or UUC triplets are often present in the target RNA. Two stretches of antisense sequence 6–8 nucleotides long that flank the 21 nucleotide sequence forming the catalytic hammerhead between them are then designed based on the target sequence surrounding the third nucleotide ("X") of the triplet. This nucleotide is not based paired with the ribozyme (Hauswirth and Lewin, *Prog. Retin. Eye Res.* 19:689–710 (2000); and Lewin and Hauswirth, *Trends. Mol. Med.* 7:221–228 (2001)).

Hairpin ribozymes also are well known in the art and can be useful in preventing or treating Crohn's disease according to a method of the invention. Hairpin ribozymes have a catalytic core of about 34 nucleotides and recognize the sequence NNYNGUCNNNNNN, where N is any nucleotide and Y is a pyrimidine. The "NGUC" sequence is not base-paired with the ribozyme. In one embodiment, a method of the invention is practiced with a hairpin ribozyme that recognizes a "NGUC" motif present, for example, in a pbrA or PFTR mRNA. In further embodiments, a method of the invention relies on a hairpin ribozyme having a tetraloop in the catalytic core rather than a 3-base loop, or a U to C substitution at position 39 of the catalytic core, or both (Hauswirth and Lewin, supra, 2000; and Lewin and Hauswirth, supra, 2001).

Target sequences, for example, in a pbrA or PFTR mRNA generally are selected to avoid secondary structures, which can interfere with the ability of a ribozyme to bind to the target site. Well-known structure-predicting algorithms can be used; in addition, potential ribozymes can be evaluated, if desired, for accessibility to hybridization with complementary sequences using, for example, a ribonuclease protection assay.

Sequence-specific ribonucleases, including ribozymes and DNA enzymes can be designed as described above and prepared by standard methods for synthesis of nucleic acid molecules. See, also, Ke et al., *Int. J. Oncol.* 12:1391–1396 (1998); Doherty et al., *Ann. Rev. Biophys. Biomol. Struct.* 30:457–475 (2001); Hauswirth and Lewin, supra, 2000; and Lewin and Hauswirth, supra, 2001. Sequence-specific ribozymes also can be identified, for example, by in vitro selection from pools of random sequences. Such methods are well known in the art, as described, for example, in Bartel and Szostak, *Science* 261:1411–1418 (1993), Breaker, *Chem. Rev.* 97:371–390 (1997) and Santoro and Joyce, *Proc. Natl. Acad. Sci., USA* 94:4262–4266 (1997)).

Where a ribozyme is to be administered to an individual directly, without being delivered using a viral or other vector, the ribozyme can be modified, if desired, to enhance stability. Modifications useful in a therapeutic ribozyme include, but are not limited to, blocking the 3' end of the molecule and the 2' positions of pyrimidines. Stabilized ribozymes having half-lives of hours can be provided by repeated doses using, for example, intravenous injection. Those skilled in the art understand that a ribozyme also can be administered by expression in a viral gene therapy vector. For example, a DNA oligonucleotide encoding the ribozyme can be cloned downstream of a RNA pol II or RNA pol III promoter and, if desired, can be embedded within the transcripts of genes such as tRNA$_{val}$, U6 snRNA or the adenoviral VA1 RNA.

The invention also provides a method of diagnosing Crohn's disease in a individual by obtaining a sample from the individual; contacting the sample with a *Pseudomonas* antigen, or an immunoreactive fragment thereof, under conditions suitable to form a complex of the *Pseudomonas* antigen, or the immunoreactive fragment thereof, and antibody to the antigen; and detecting the presence or absence of the complex, where the antigen is not the I-2 antigen, and where presence of the complex indicates that the individual has Crohn's disease. In such a diagnostic method of the invention, the presence or absence of the complex can be detected, for example, with a detectable secondary antibody.

The invention additionally provides a method of diagnosing Crohn's disease in a individual by obtaining a sample from the individual; contacting the sample with pbrA, or an immunoreactive fragment thereof, under conditions suitable to form a complex of pbrA, or the immunoreactive fragment thereof, and antibody to pbrA; and detecting the presence or absence of the complex, where the presence of the complex indicates that the individual has Crohn's disease. In such a diagnostic method of the invention, the presence or absence of the complex can be detected, for example, with a detectable secondary antibody. In a method of the invention, the pbrA can have, for example, the amino acid sequence SEQ ID NO: 2 or SEQ ID NO: 3, or an immunoreactive fragment of one of these sequences.

The invention also provides a method of diagnosing Crohn's disease in a individual by obtaining a sample from the individual; contacting the sample with PFTR, or an immunoreactive fragment thereof, under conditions suitable to form a complex of PFTR, or the immunoreactive fragment thereof, and antibody to PFTR; and detecting the presence or absence of the complex, provided that the immunoreactive fragment is not I-2 or a fragment thereof, and where the presence of the complex indicates that the individual has Crohn's disease. In one embodiment, the presence or absence of the complex is detected with a detectable secondary antibody. In a further embodiment, the PFTR has the amino acid sequence SEQ ID NO: 5, or an immunoreactive fragment thereof.

A sample useful in the diagnostic methods of the invention can be obtained from any biological fluid having antibodies such as, for example, whole blood, serum, plasma, saliva, or other bodily fluid or tissue.

A *Pseudomonas* antigen useful in the invention can be purified, partially purified or present in a whole or fractionated *Pseudomonas* cellular extract. If desired, for example, *Pseudomonas*, such as *P. fluorescens*, can be cultured and then pelleted and washed by repetitive centrifugation and resuspension in buffer. The cultured bacteria can be grown to various stages of culture maturity such as early log phase, late log phase, etc. After a final centrifugation, the bacterial pellet can be lysed, for example, by sonication; chemical methods including the use of ionic or non-ionic detergents, or enzymatic methods (lysozyme), can be used to release the intracellular components in a small volume. The cellular debris can be vigorously sonicated to disrupt associated intracellular components.

After the bacterial components are concentrated, the cellular debris can be fractionated by chromatographic techniques based on, for example, molecular size, isoelectric point, binding properties, or other physical characteristics to yield a crude separation of sub-cellular components in groups or peaks. Although not completely pure, fractions containing individual partially purified preparations of the cellular components including proteins, saccharides and lipids, can be screened on ELISA plates. For example, individual (or groups of) peaks can be diluted and assayed for immunoreactivity against a single pool of sera from known Crohn's disease patients and a control pool of sera from known non-IBD patients. Substantial reactivity observed in the pool of Crohn's disease sera with little or no reactivity in the non-IBD patient pool indicates a useful *Pseudomonas* antigen preparation. If desired, a panel of individual patient samples including patients confirmed with Crohn's disease, ulcerative colitis, non-IBD disease controls, and healthy, asymptomatic controls can be screened against the antigenic preparation. If necessary, fractions containing reactivity mixtures can be further sub-fractionated in the same way to identify antigenic preparations of higher purity.

As used herein, the term "complex" is synonymous with "immune complex" and means an aggregate of two or more molecules that results from specific binding between an antigen, such as a protein or peptide, and an antibody. In the methods of the invention, a complex is formed by specific binding of a *Pseudomonas* antigen such as pbrA or PFTR to an antibody.

In the methods of the invention, a complex can be detected with a detectable secondary antibody that has specificity for a class determining portion of the antibody to the *Pseudomonas* antigen. Such a secondary antibody can be, for example, an anti-IgA secondary antibody, an anti-IgG secondary antibody, or a combination of anti-IgA and anti-IgG secondary antibodies.

As used herein, the term "secondary antibody" means an antibody or combination of antibodies, which binds an antibody that specifically binds a *Pseudomonas* antigen. One skilled in the art understands that, preferably, a secondary antibody does not compete with the antigen for binding to the primary antibody. A secondary antibody can bind any epitope of the antibody that specifically binds the *Pseudomonas* antigen. A particularly useful secondary antibody is an anti-IgA or anti-IgG antibody having specificity for the class determining portion of the primary antibody. A useful secondary antibody is specific for the species from which the sample was obtained. For example, if human serum is the sample to be assayed, mouse anti-human IgA or IgG can be a useful secondary antibody. A combination of different antibodies, which can be useful in the methods of the invention, also is encompassed within the meaning of the term secondary antibody, provided that at least one antibody of the combination reacts with an antibody that specifically binds a *Pseudomonas* antigen.

A secondary antibody useful in the invention can be obtained commercially or by techniques well known in the art. Such an antibody can be a polyclonal or monoclonal antibody. For example, IgG reactive polyclonal antibodies can be prepared using IgG or Fc fragments of IgG as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988). Monoclonal secondary antibodies, which are a population of antibody molecules that contain only one species of idiotype capable of binding a particular antigen epitope, also can be produced by routine methods or obtained commercially.

The term "detectable secondary antibody" means a secondary antibody, as defined above, that can be detected or measured by analytical methods. Thus, the term secondary antibody includes an antibody labeled directly or indirectly with a detectable marker that can be detected or measured and used in a convenient assay such as an enzyme-linked immunosorbent assay, radioimmunoassay, radial immunodiffusion assay or Western blotting assay. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to the *Pseudomonas* antigen. If desired, a multiple antibody system can be used as the secondary antibody as discussed above. In such a system, at least one of the antibodies is capable of binding the primary antibody and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm. A urease detection system also can be used in the methods of the invention, for example, with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgG-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine, for example, are fluorochromes that can be linked to a secondary antibody and used to detect the presence or absence of a complex in a method of the invention. In particular embodiments, the fluorochrome is fluorescein or rhodamine. Methods of conjugating and using these and other suitable fluorochromes are described, for example, in Van Vunakis and Langone, *Methods in Enzymology*, Volume 74, Part C (1991). A secondary antibody linked to a fluorochrome also can be obtained from commercial sources. For example, goat F(ab')₂ anti-human IgG-FITC is available from Tago Immunologicals (Burlingame, Calif.).

A secondary antibody also can be labeled with a chemiluminescent marker. Such a chemiluminescent secondary antibody is convenient for sensitive, non-radioactive detection of a complex containing pbrA or PFTR and can be obtained commercially from various sources such as Amersham Lifescliences, Inc. (Arlington Heights, Ill.).

A secondary antibody further can be rendered detectable by labeling with a radioisotope. An iodine-125 labeled secondary antibody is a particularly useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The assays of the present invention can be forward, reverse or simultaneous as described in U.S. Pat. No. 4,376,110, issued Mar. 8, 1983, to David et al. In the forward assay, each reagent is sequentially contacted with the purified Pseudomonas antigen such as pbrA or PFTR. If desired, separation of bound from unbound reagent can be performed before the addition of the next reagent. In a reverse assay, all reagents are pre-mixed prior to contacting with the Pseudomonas antigen. A modified reverse assay is described in U.S. Pat. No. 4,778,751 issued Oct. 18, 1988, to El Shami et al. In a simultaneous assay, all reagents are separately but contemporaneously contacted with a Pseudomonas antigen such as pbrA or PFTR.

Separation steps for the various assay formats described herein, including the removal of unbound secondary antibody from the complex, can be performed by methods known in the art (Harlow and Lane, supra, 1988). For example, washing with a suitable buffer can be followed by filtration, aspiration or magnetic separation. If the Pseudomonas antigen or immunoreactive fragment thereof is immobilized on a particulate support, such as on microparticles, the particulate material can be centrifuged, if desired, followed by removal of wash liquid. If the Pseudomonas antigen or an immunoreactive fragment thereof is immobilized on a membrane, filter or well, a vacuum or liquid absorbing apparatus can be applied to the opposite side of the membrane, filter or well to draw the wash liquid away from the complex.

As described above, immunoreactive and tolerogenic fragments of Pseudomonas antigens such as pbrA and PFTR also are useful in the invention. The term "immunoreactive fragment," as used in reference to pbrA, means a peptide or polypeptide portion of pbrA that has immunoreactivity as defined by the ability of an anti-pbrA antibody-positive sample to form a complex with the pbrA polypeptide. Similarly, the term "immunoreactive fragment," as used in reference to PFTR, means a peptide or polypeptide portion of PFTR that has immunoreactivity as defined by the ability of an anti-PFTR antibody-positive sample to form a complex with the PFTR polypeptide. Thus, the term "immunoreactive fragment of pbrA" as used herein, means a peptide or polypeptide that has an amino acid sequence that is substantially the same as a portion of the amino acid sequence provided as SEQ ID NO: 2 or SEQ ID NO: 3 and immunoreactivity as defined by the ability to form a complex with an anti-pbrA antibody-positive sample such as a pbrA-reactive serum sample from a Crohn's disease patient. Similarly, the term "immunoreactive fragment of PFTR," as used herein, means a peptide or polypeptide that has an amino acid sequence that is substantially the same as a portion of the amino acid sequence provided as SEQ ID NO: 5 and immunoreactivity as defined by the ability to form a complex with an anti-PFTR antibody-positive sample such as a PFTR-reactive serum sample from a Crohn's disease patient.

In general, an immunoreactive fragment has from about three amino acids to the full-length of pbrA or PFTR. An immunoreactive fragment of pbrA or pFTR can have, for example, at least 5, 8, 10, 12, 15, 18, 20 or 25 amino acids. For example, an immunoreactive fragment of pbrA or PFTR can be from five to fifty amino acids, from eight to fifty amino acids, or from ten to fifty amino acids in length, or can be, for example, from eight to twenty amino acids or from ten to twenty amino acids in length, or can be, for example, from twelve to twenty amino acids or from fifteen to twenty amino acids in length.

An immunoreactive fragment of a pbrA polypeptide can be identified by the ability to form a complex with a pbrA-reactive sample, for example, a pbrA reactive CD patient serum sample. Similarly, an immunoreactive fragment of a PFTR polypeptide can be identified by the ability to form a complex with a PFTR-reactive sample, for example, a PFTR reactive CD patient serum sample. Assays for the formation of a complex between an antigen and a serum sample are disclosed herein and well known in the art. An ELISA assay can be particularly useful in identifying an immunoreactive fragment of pbrA or PFTR or another Pseudomonas antigen.

Tolerogenic and immunoreactive fragments of Pseudomonas antigens such as pbrA or PFTR also can be useful in the methods of the invention. The term "tolerogenic fragment" means a peptide or polypeptide portion of the polypeptide that has tolerogenic activity as defined by its ability either alone, or in combination with another molecule, to produce a decreased immunological response. Thus, a tolerogenic fragment of a pbrA polypeptide is a peptide or polypeptide that has substantially the same amino acid sequence as a portion of SEQ ID NO: 2 or SEQ ID NO: 3 and tolerogenic activity as defined by its ability either alone, or in combination with another molecule, to produce a decreased immunological response. Similarly, a tolerogenic fragment of a PFTR polypeptide is a peptide or polypeptide that has substantially the same amino acid sequence as a portion of SEQ ID NO: 5 and tolerogenic activity as defined by its ability either alone, or in combination with another molecule, to produce a decreased immunological response.

A tolerogenic fragment can have from about three amino acids to the full length of pbrA or PFTR. A tolerogenic fragment can have, for example, at least 5, 8, 10, 12, 15, 18, 20 or 25 amino acids of pbrA or PFTR. For example, a tolerogenic fragment can have from five to fifty amino acids, from eight to fifty amino acids, or from ten to fifty amino acids; from eight to twenty amino acids or from ten to twenty amino acids; or from twelve to twenty amino acids or from fifteen to twenty amino acids.

A tolerogenic fragment of a pbrA or PFTR polypeptide can be identified using a variety of assays, including in vitro assays such as T-cell proliferation or cytokine secretion assays and in vivo assays such as the induction of tolerance in murine models of inflammatory bowel disease. T-cell proliferation assays, for example, are well recognized in the art as predictive of tolerogenic activity (see, for example, Miyahara et al., *Immunol.* 86:110–115 (1995) or Lundin et al, *J. Exp. Med.* 178:187–196 (1993)). A T-cell proliferation assay can be performed by culturing T-cells with irradiated antigen-presenting cells, such as normal spleen cells, in microtiter wells for 3 days with varying concentrations of the fragment of pbrA or PFTR to be assayed; adding $^3$H-thymidine; and measuring incorporation of $^3$H-thymidine into DNA. In such an assay, a fragment of pbrA or PFTR can be tested for activity, for example, at concentrations of 20 µg/ml and 40 µg/ml.

A tolerogenic fragment also can be identified using a T-cell cytokine secretion assay known in the art. For example, T cells can be cultured with irradiated antigen-presenting cells in microtiter wells with varying concentrations of the fragment of interest and, after three days, the culture supernatants can be assayed for IL-2, IL-4 or IFN-γ as described in Czerinsky et al., *Immunol. Rev.* 119:5–22 (1991).

Primary T-cells for use in a T-cell proliferation assay or cytokine secretion assay, for example, can be isolated from lamina propria or peripheral blood. In addition, a convenient source of T-cells for use in an in vitro assay for tolerogenic activity can be a T-cell line established from an IBD patient such as a Crohn's disease patient, from a murine model of IBD or from a healthy animal immunized with *P. fluorescens*. A preferred source of T-cells for use in identifying a tolerogenic fragment is a Crohn's disease patient.

A T-cell line can be established from a patient with CD or UC, for example, by culturing T lymphocytes with about 1 µg/ml recombinant pbrA or PFTR, in the presence of low concentrations of growth-supporting IL-2 (about 10 µg/ml). A T-cell line can be established by culturing T lymphocytes with antigen-presenting cells and feeding the cells on an alternating four to five day cycle with either IL-2 and pbrA or PFTR or IL-2 alone as described in Nanda et al., *J. Exp. Med.* 176:297–302 (1992). A cell line that develops into a reliably proliferating cell line dependent on the presence of pbrA or PFTR is particularly useful in identifying tolerogenic fragments. The establishment of T-cell lines from small intestinal mucosa is described, for example, in Lundin et al., supra, 1993. T cell lines dependent upon the presence of pbrA or PFTR can be useful for identifying tolerogenic fragments useful in the methods of the invention.

A tolerogenic fragment of pbrA or PFTR also can be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of pbrA or PFTR, for example, and a T-cell response or anti-pbrA or anti-PFTR antibody titer can be assayed after challenging by immunization. For example, a neonatal mouse can be tolerized within 48 hours of birth by intraperitoneal administration of about 100 µg of a fragment of pbrA or PFTR emulsified with incomplete Freund's adjuvant and subsequently immunized with pbrA or PFTR at about 8 weeks of age (see, for example, Miyahara, supra, 1995). An adult mouse can be tolerized intravenously with about 0.33 mg of a fragment of a *Pseudomonas* antigen such as pbrA or PFTR, administered daily for three days (total dose 1 mg), and immunized one week later with pbrA or PFTR. A decreased T-cell response, such as decreased proliferation or cytokine secretion, which indicates tolerogenic activity, can be measured using T-cells harvested 10 days after immunization. In addition, a decreased anti-pbrA or anti-PFTR antibody titer, which also indicates tolerogenic activity, can be assayed using blood harvested 4–8 weeks after immunization. Methods for assaying a T-cell response or antibody titer are described above and are well known in the art.

A tolerogenic fragment also can be identified using a murine model of inflammatory bowel disease. Neonatal or adult mice having IBD-like disease can be tolerized with a fragment of pbrA or PFTR as described above, and the T-cell response or antibody titer assayed. A decreased T-cell response or decreased antibody titer to the antigen indicates a decreased immunological response and, thus, serves to identify a tolerogenic fragment of pbrA or PFTR. In addition, a tolerogenic fragment of pbrA or PFTR can be identified by the ability to reduce the frequency, time of onset or severity of colitis in a murine model of IBD.

Several well-accepted murine models of inflammatory bowel disease can be useful in identifying a tolerogenic fragment useful in the invention. For example, mice with target disruption of the genes encoding the alpha subunit of the G-protein Gi2, are a well known model exhibiting features of human bowel disease (Hornquist et al., *J. Immunol.* 158:1068–1077 (1997); Rudolph et al., *Nat. Genet.* 10:143–150 (1995)). Mice deficient in IL-10 as described in Kühn et al., *Cell* 75:263–274 (1993), and mice deficient in IL-2 as described in Sadlack et al., *Cell* 75:253–261 (1993), also have colitis like disease and are useful in identifying a tolerogenic fragment useful in the invention. Furthermore, mice with mutations in T cell receptor (TCR) α, TCR β, TCR β×δ, or the class II major histocompatiblility complex (MHC) as described in Mombaerts et al., *Cell* 75:275–282 (1993), develop inflammatory bowel disease and, thus, are useful in identifying a tolerogenic fragment of pbrA or PFTR. Similarly, a fragment can be assayed for tolerogenic activity in a SCID mouse reconstituted with CD45RB CD4+ T-cells, which is a well-accepted model of inflammatory bowel disease, as described in Powrie et al., *Immunity* 1:553–562 (1994). Additional animal models of IBD also are well known in the art (see, for example, Podolsky, *Acta Gastroenterol. Belg.* 60:163–165 (1997); and Bregenholt et al., APMIS 105: 655–662 (1997)). Thus, a tolerogenic fragment of pbrA or PFTR can be readily identified by an in vitro or in vivo assay disclosed herein or by another assay well known in the art.

An immunoreactive or tolerogenic fragment can be identified by screening a large collection, or library, of peptides of interest or random peptides for immunoreactivity or tolerogenic activity. For example, a panel of peptides spanning the entire sequence of a pbrA polypeptide such as SEQ ID NO: 2 or SEQ ID NO: 3, or a PFTR polypeptide such as SEQ ID NO: 5, can be screened for immunoreactivity or tolerogenic activity as described above. Such a panel can be a panel of 15-mer peptides spanning SEQ ID NO: 2, SEQ ID NO: 3 or SEQ ID NO: 5, each overlapping by three or five residue shifts using the Mimotope cleavable pin technology (Cambridge Research Biochemicals, Wilmington, Del.), as described by Geysen et al., *Science* 235:1184 (1987). The panel is subsequently screened for immunoreactivity or tolerogenic activity using one of the assays described above (see, for example, Miyahara et al., supra, 1995). A library of peptides to be screened also can be a population of peptides related in amino acid sequence to SEQ ID NO: 2 but having one or more amino acids that differ from SEQ ID NO: 2, or can be a library of peptides related in amino acid sequence to SEQ ID NO: 5 but having one or more amino acids that differ from SEQ ID NO: 5.

Additional peptides to be screened include, for example, tagged chemical libraries of peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149). These or other well known methods can be used to produce a phage display library which can be screened, for example, with one of the disclosed assays for immunoreactivity or tolerogenic activity. If desired, a population of peptides can be assayed for activity en masse. For example, to identify an immunoreactive fragment of pbrA, a population of peptides can be assayed for the ability to form a complex with a sample containing anti-pbrA reactivity; the active population can be subdivided and the assay repeated in order to isolate the immunoreactive fragment from the population.

An immunoreactive or tolerogenic fragment also can be identified by screening, for example, fragments of the polypeptide produced by chemical or proteolytic cleavage. Methods for chemical and proteolytic cleavage and for purification of the resultant protein fragments are well known in the art (see, for example, Deutscher, *Methods in Enzymology*, Vol. 182, "Guide to Protein Purification," San Diego: Academic Press, Inc. (1990)). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of pbrA or PFTR that can be screened for immunoreactivity or tolerogenic activity using one of the assays disclosed herein.

A purified *Pseudomonas* antigen, or an immunoreactive or tolerogenic fragment thereof, can be produced or synthesized using methods well known in the art. Such methods include recombinant DNA methods and chemical synthesis methods for production of a peptide. Recombinant methods of producing a peptide or protein through expression of a nucleic acid sequence in a suitable host cell are well known in the art and are described, for example, in Sambrook et al., *Molecular Cloning: A Laboratory Manual*, 2nd Ed, Vols 1 to 3, Cold Spring Harbor Laboratory Press, New York (1989). The sequence of a nucleic acid molecule encoding pbrA and PFTR are disclosed herein as SEQ ID NOS: 1 and 4, respectively.

Purified antigens and immunoreactive and tolerogenic fragments thereof also can be produced by chemical synthesis, for example, by the solid phase peptide synthesis method of Merrifield et al., *J. Am. Chem. Soc.* 85:2149 (1964). Standard solution methods well known in the art also can be used to synthesize an immunoreactive or tolerogenic fragment useful in the invention (see, for example, Bodanszky, *Principles of Peptide Synthesis*, Springer-Verlag, Berlin (1984) and Bodanszky, *Peptide Chemistry*, Springer-Verlag, Berlin (1993)). A newly synthesized peptide can be purified, for example, by high performance liquid chromatography (HPLC), and can be characterized using, for example, mass spectrometry or amino acid sequence analysis.

The following examples are intended to illustrate but not limit the present invention.

EXAMPLE I

Identification of a Microbial Organism Involved in Crohn's Disease

This example describes identification of *P. fluorescens* as a microbial organism that can play a role in the etiology of Crohn's disease.

Clinical isolates representing 14 bacterial species within the *Pseudomonadaceae* family were obtained the from UCLA Clinical Laboratories. These were screened by genomic PCR for the I-2 sequence essentially as described in Sutton et al., *Gastroenterology* 119:23–28 (2000). These same sample were also assayed by Southern analysis of genomic DNA using a 300 bp probe containing nucleotides 117 to 418 of the sequence shown as SEQ ID NO: 4.

Of the 14 species assayed, four (*P. Aeruginosa, P. pseudoalcaligenes, P. fluorescens* and *Shewanella putrefasciens*) were positive by Southern analysis. Only the sample from *P. fluorescens* was positive by PCR. Sequencing of the amplified PCR product from *P. fluorescens* indicated that it was identical to the I-2 sequence, which has been characterized as being preferentially present in involved Crohn's disease (CD) mucosa as compared to uninvolved mucosa.

These results demonstrate that the exact I-2 gene exists in the *P. fluorescens* genome and that homologs of I-2 exist in 4 of 14 *Pseudomonadaceae* family members including PA2885 of *P. aeruginosa*. These results further indicate that *P. fluorescens* is a microbial organism that can play a role in the etiology of Crohn's disease.

EXAMPLE II

Pathogenic Role of *Pseudomonas Fluorescens* in a Mouse Colitis Model

This example demonstrates a pathogenic role for *P. fluorescens* in the CD4+CD45RBhi mouse model of colitis.

The CD4+CD45RBhi mouse model of Crohn's disease displays a requirement for enteric bacteria as a pathogenic cofactor for colitis. This requirement for enteric bacteria is a critical feature shared with human Crohn's disease (Martin and Rhodes, *Curr. Opin. Infect. Dis.* 13:503–509 (2000)). While a complete mixture of intestinal microbiota (cecal lumenal contents) results in colitis in CD4+CD45RBhi mice, introduction of individual prominent bacterial species cannot substitute for the complete mixture and is ineffective at initiating disease. Thus, only particular bacteria, which may be minor components of the intestinal microbiota, express the traits required for inducing Crohn's disease in susceptible individuals.

*P. fluorescens* was tested for the ability to act as a pathogenic cofactor in CD4+CD45RBhi mice. The mice were prepared using either CB.17scid or C57B1/6 [RAG1−/−] recipients, adoptively transferred with 5 X 106 CD4+CD45RBhi T cells from the wildtype syngenic strain, following a standard protocol (Aranda et al., *J. Immunol.* 158:3464–3473 (1997)). In particular, $1 \times 10^9$ *P. fluorescens* were introduced by a single gastric gavage. Within the first week of bacterial administration, ten of 12 CD4+CD45RBhi mice died. In contrast, no disease was observed in any of 12 normal control mice over a month of surveillance, even with further weekly bacterial administration.

These results indicate that *P. fluorescens*, unlike typical intestinal microflora, can be pathogenic in colitis-susceptible individuals. These results further indicate that vaccines and agents that reduce or eradicate *P. fluorescens* can be useful for the treatment and prevention of Crohn's disease.

EXAMPLE III

Additional *Pseudomonas* Antigenic Targets

Figure 1:
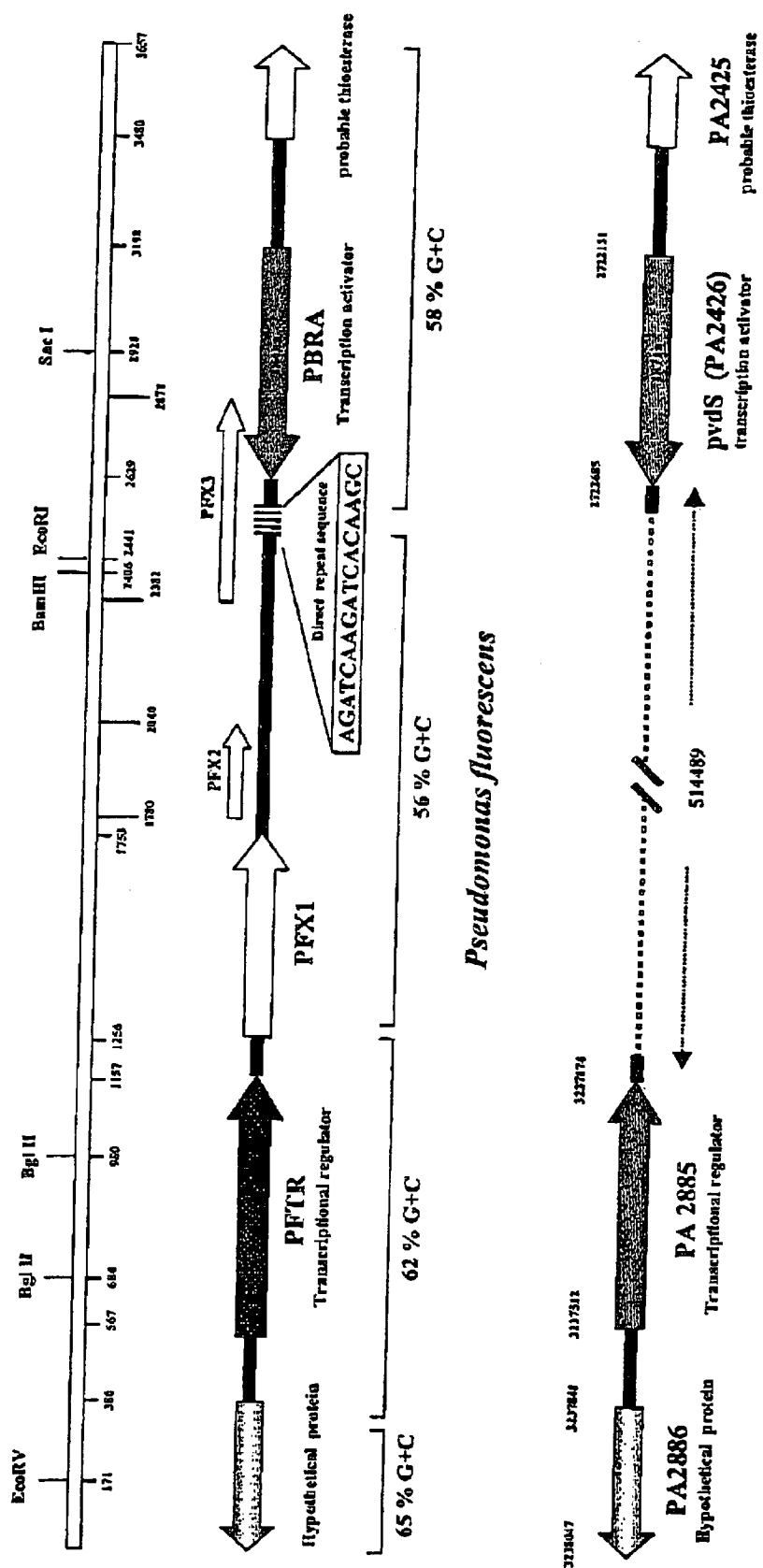
FIG. 1 shows a comparison of homologous genomic regions in *P. aeruginosa* and *P. fluorescens*. The top of the FIG. lists predicted restriction enzyme sites and nucleotide numbering beginning at the 5' end of the cloned *P. fluorescens* sequence. Numbering of the homologous region of *P. aeruginosa* corresponds to the genomic nucleotide position. A direct hexamer repeat (eleven repeats) within PFX3 of *P. fluorescens* is also indicated (nucleotide position 2473 to 2565; AGATCAAGATCACAAGC; SEQ ID NO: 6).

This example describes identification of *Pseudomonas* antigens useful in diagnosing and treating Crohn's disease.
pbrA is a Conserved *Pseudomonas Fluorescens* Antigen RACE cloning of PFTR flanking sequence disclosed a previously undefined locus in *P. fluorescens*; the homologous region in *P. aeruginosa* was identified by BLAST analysis, from the recently reported genome (Stover et al., CITATION, 2000). As shown in FIG. 1, *P. fluorescens* and *P. aeruginosa* were homologous for several colinear open reading frames. Cloning of the region upstream of PFTR revealed a hypothetical open reading frame (ORF), which was homologous to a PA2886, a novel ORF in the same genomic position relative to PA2885 in *P. aeruginosa*.

Cloning of the region downstream of PFTR disclosed several notable elements. A previously reported iron-regulated transcription factor, pbrA, was present in *P. fluorescens* (Sexton et al., *Mol. Gen. Genet.* 250:50–58 (1996)). In *P. aeruginosa*, this genomic position was occupied by pvdS, a homologous iron starvation sigma factor; the pbrA sequence also was homologous to the pfrI gene in *P. putida* (Wilson et al., *J. Bacteriol.* 183:2151–2155 (2001); Leoni et al., *J. Bacteriol.* 182:1481–1491 (2000)). A comparison of pbrA from *P. fluorescens* (pbrA-v; UCLA #268) with pvdS and pfrI is shown in FIG. 2. Strong conservation was revealed across the protein sequences, with the exception of a divergent C-terminal region.

These results indicate that pbrA is a *P. fluorescens* specific protein that can be useful in diagnosis as well as in pharmacologic or vaccine targeting of *P. fluorescens* in Crohn's therapy.
PFTR Enzymatic Function Sequence analysis of the pftr coding region identified several conserved motifs indicative of pftr enzymatic function. The pftr sequence was compared to the Prosite database found on the ExPASy Molecular Biology Server. Scanning results revealed two 2Fe-2S ferredoxin iron-sulfur binding domains (see FIG. 4), indicating that PFTR has ferredoxin activity. These results indicate that inhibitors or agents that disrupt PFTR ferrodoxin activity can be used as therapeutics for treatment of Crohn's disease.

The *P. fluorescens* Protein PFTR Stimulates CD4+ T-Cell Proliferation

The previously identified I-2 sequence represents the central portion of the *P. fluorescens* protein (PFTR), which is homologous to the *P. aeruginosa* homologue PA2885.

The full-length parent protein (PFTR), and the *P. aeruginosa* homologue (PA2885) were assayed for the ability to stimulate CD4+ T cell proliferation. A His-tagged protein expression vector was used to express I-2, PFTR, and PA2885, and the recombinant proteins purified by nickel chromatography. Each protein was preincubated with antigen-presenting cells, and tested for the ability to stimulate CD4+ T cell proliferation. As illustrated in FIG. 3, both I-2 and PFTR strongly stimulated CD4+ T-cell proliferation to a similar extent. Furthermore, the cell proliferation response observed with either I-2 or PFTR was similar to the superantigen control (SEB). In contrast, the *P. aeruginosa* homologue PA2885 was much less active in stimulating T cell proliferation. These results indicate that PFTR induces CD4+ T cell proliferation and that sequence polymorphisms between PFTR and PA2885 can define sequences important for this activity.

The I-2 protein activates murine T cells in a manner indicative of a T cell superantigen (Dalwadi, CITATION, 2001). Such T cell superantigens are an important virulence trait of certain pathogenic bacteria, due to direct and indirect tissue damage mediated by a cognately activated T cell population (Li et al., *Annu. Rev. Immunol.* 17:435–466 (1999); Marrack and Kappler, *Cell* 76:323–332 (1994)). Among species known to express T cell superantigens, gram-negative bacteria are notably absent, with the exception of an apparent T cell superantigen in *Yersinia pseudotuberculosis* (Abe et al., *J. Clin. Invest.* 99:1823–1830 (1997)).

These results indicate that PFTR is a member of a distinct structural class of T cell superantigens and that *P. fluorescens* is an unusual gram-negative intestinal commensal that has T-cell superantigen activity. The modest immunoactivity of the *P. aeruginosa* homologue, PA 2885, indicates that *P. aeruginosa* is unlikely to express significant T cell superantigen activity and further indicates that vaccines or therapeutic agents directed against *P. fluorescens* can be particularly useful in preventing or treating Crohn's disease.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of diagnosing Crohn's disease in a individual, comprising:

(a) contacting a sample from said individual with pbrA, or an immunoreactive fragment thereof, under conditions suitable to form a complex of pbrA, or said immunoreactive fragment thereof, and antibody to pbrA; and (b) detecting the presence or absence of said complex, wherein the presence of said complex indicates that said individual has Crohn's disease, said pbrA having greater than 70% amino acid sequence identity with SEQ ID NO: 2 or SEQ ID NO: 3 and wherein said pbrA is purified, partially purified or present in a whole or fractionated *Pseudomonas* cellular extract.

2. The method of claim 1, wherein the presence or absence of said complex is detected with a detectable secondary antibody.

3. The method of claim 1, wherein said pbrA or an immunoreactive fragment thereof is purified.

4. The method of claim 1 or 3, wherein said pbrA has greater amino acid sequence similarity to SEQ ID NO: 2 or SEQ ID NO: 3 than to the *P. aeruginosa* protein pvds (SEQ ID NO: 7).

5. The method of claim 1 or 3, wherein said pbrA has the amino acid sequence of SEQ ID NO: 2 or an immunoreactive fragment thereof.

6. The method of claim 5, wherein said pbrA has the amino acid sequence of SEQ ID NO: 2.

7. The method of claim 1 or 3, wherein said pbrA has the amino acid sequence of SEQ ID NO: 3 or an immunoreactive fragment thereof.

8. The method of claim 7, wherein said pbrA has the amino acid sequence of SEQ ID NO: 3.

\* \* \* \* \*